(12) United States Patent
Fujioka et al.

(10) Patent No.: US 12,735,742 B2
(45) Date of Patent: Sep. 15, 2026

(54) COMPOSITION FOR NUCLEIC ACID ANALYSIS, NUCLEIC ACID ANALYZING METHOD, AND NUCLEIC ACID ANALYZER

(71) Applicant: HITACHI HIGH-TECH CORPORATION, Tokyo (JP)

(72) Inventors: Michiru Fujioka, Tokyo (JP); Yusuke Goto, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 982 days.

(21) Appl. No.: 17/924,018

(22) PCT Filed: May 29, 2020

(86) PCT No.: PCT/JP2020/021273
§ 371 (c)(1),
(2) Date: Nov. 8, 2022

(87) PCT Pub. No.: WO2021/240761
PCT Pub. Date: Dec. 2, 2021

(65) Prior Publication Data
US 2023/0175056 A1 Jun. 8, 2023

(51) Int. Cl.
*C12Q 1/6869* (2018.01)
*G01N 27/447* (2006.01)

(52) U.S. Cl.
CPC ..... *C12Q 1/6869* (2013.01); *G01N 27/44791* (2013.01)

(58) Field of Classification Search
CPC ............................ C12Q 1/6869; C12Q 1/6806
See application file for complete search history.

(56) References Cited

U.S. PATENT DOCUMENTS

2010/0035260 A1 2/2010 Olasagasti et al.
2013/0327644 A1 12/2013 Turner et al.
2016/0319344 A1 11/2016 Croquette et al.
2021/0293750 A1 9/2021 Akahori et al.

FOREIGN PATENT DOCUMENTS

GB 2603061 A * 7/2022 ........... C12Q 1/6876
JP 2017-500046 A 1/2017
JP 2020-031557 A 3/2020
WO WO-2010117470 A2 * 10/2010 ........... G01N 27/447

OTHER PUBLICATIONS

Gerald M. Cherf, et al., "Automated forward and reverse ratcheting of DNA in a nanopore at 5-A precision", Nature biotechnology, vol. 30, No. 4, pp. 344-348, Apr. 2012.
Clive Brown, Nanopore Community Meeting 2019 technology update., https://nanoporetech.com/resource-centre/nanopore-community-meeting-2019-technology-update.
International Search Report of PCT/JP2020/021273 dated Aug. 11, 2020.

* cited by examiner

*Primary Examiner* — Young J Kim
(74) *Attorney, Agent, or Firm* — MATTINGLY & MALUR, PC

(57) ABSTRACT

In a base sequence determination system that performs a complementary strand synthesis reaction of a template DNA strand using DNA polymerase, a complementary strand synthesized by DNA polymerase is degraded by exonuclease in a solution.

8 Claims, 19 Drawing Sheets

COMPOSITION FOR NUCLEIC ACID ANALYSIS, NUCLEIC ACID ANALYZING METHOD, AND NUCLEIC ACID ANALYZER

TECHNICAL FIELD

The present invention relates to a composition for nucleic acid analysis that is used for nucleic acid analysis using a nucleic acid synthesis reaction by polymerase, a nucleic acid analyzing method using a nucleic acid synthesis reaction by polymerase, and a nucleic acid analyzer.

BACKGROUND ART

As a device for determining the monomer sequence (base sequence) of a nucleic acid molecule, a method of electrically measuring the base sequence of DNA directly without performing extension reactions or fluorescence labeling has attracted attention. More specifically, a so-called nanopore DNA sequencing method of determining a base sequence by directly measuring a DNA strand is known.

In this nanopore DNA sequencing method, a base sequence is measured by measuring a blocking current generated when a DNA strand passes through a nano-sized pore (hereinafter, referred to as "nanopore") formed in a membrane. That is, the blocking current changes depending on a difference between individual base types in a DNA strand. Therefore, by measuring the amount of the blocking current, the base types can be sequentially identified. In this method, unlike various sequencers described above, it is not necessary to perform an amplification reaction by an enzyme in which a DNA strand is used as a template or to add a label such as a fluorescent substance. Therefore, the nanopore DNA sequencing method has a higher throughput and a lower running cost than various sequencers in the related art, and enables long-base DNA decoding.

In general, this nanopore DNA sequencing method is implemented by a device for biomolecular analysis including: first and second liquid tanks that are filled with an electrolytic solution; a membrane that separates the first and second liquid tanks and includes a nanopore; and first and second electrodes provided in the first and second liquid tanks. The device for biomolecular analysis can also be configured as an array device. The array device refers to a device including plural sets of liquid chambers that are separated by the membrane. For example, a common tank can be used as the first liquid tank, and a plurality of individual tanks can be used as the second liquid tank. In this case, an electrode is disposed in each of the common tank and the individual tanks.

In this configuration, a voltage is applied between the first liquid tank and the second liquid tank, and an ionic current corresponding to a nanopore size flows through the nanopore. In addition, a potential gradient corresponding to the applied voltage is formed in the nanopore. When a biomolecule is introduced into the first liquid tank, the biomolecule is transported to the second liquid tank through the nanopore according to a diffusion phenomenon and the formed potential gradient. The size of the ionic current is proportional to a cross-sectional area of the nanopore by primary approximation. When DNA passes through the nanopore, DNA blocks the nanopore, and the effective cross-sectional area decreases, and thus the ionic current decreases. This current is called the blocking current. Based on the size of the blocking current, a difference between a single-stranded DNA and a double-stranded DNA or the type of a base is discriminated.

In addition, a method is also known in which, by providing a pair of probe electrodes on inner side surfaces of the nanopore and the like to face each other and applying a voltage between the electrodes, a tunneling current generated between DNA and the probe electrodes during passage through the nanopore is measured to discriminate the type of a base based on the size of the tunneling current.

One object of the nanopore DNA sequencing method is, for example, a transport control of DNA that passes the nanopore. In order to measure a difference between the types of individual bases in a DNA strand based on the amount of the blocking current, it is presumed that the nanopore passage speed of DNA needs to be 100 μs or faster per base due to a current noise and a time constant of fluctuation of DNA molecules during the measurement. However, the nanopore passage speed of DNA is typically fast at 1 μs or less per base, and it is difficult sufficiently measure the blocking current derived from each of the bases.

As one transport control method, there is a method of using a force to transport and control a single-stranded DNA as a template when DNA polymerase carries out a complementary strand synthesis reaction (for example, refer to NPL 1). DNA polymerase binds to DNA as a template such that the complementary strand synthesis reaction is carried out from an end portion of a primer complementarily binding to the template DNA. In the first liquid tank, DNA polymerase carries out the complementary strand synthesis reaction in the vicinity of the nanopore such that the template DNA is transported to the second liquid tank through the nanopore. This DNA polymerase is called a molecular motor.

Currently, as an actual device to which the nanopore DNA sequencing method is applied, a device using a chip where a nanopore formed of protein is disposed on a polymer membrane that prevents the flow of a current is known. In this device, when a DNA strand to be analyzed is introduced into the first liquid tank, a single-stranded DNA is transported to the second liquid tank through the nanopore formed of protein. NPL 2 discloses a technique of causing nuclease to be present in the second liquid tank of the device, degrading the transported single-stranded DNA, and preventing the single-stranded DNA from forming a steric structure in the second liquid tank.

On the other hand, as a method of measuring the base sequence of DNA that is different from the nanopore DNA sequencing method, a single-molecule real-time sequencing method is known. In the single-molecule real-time sequencing method, a complementary strand synthesis reaction is carried out by DNA polymerase fixed in a pore by using circular DNA including DNA to be analyzed as a template and using fluorescence-labeled nucleotide as a substrate. In the single-molecule real-time sequencing method, excitation light is irradiated from the bottom surface of the pore. The pore has a small size where transmission of a visible light ray having a wavelength of up to 600 nm is not allowed. Therefore, only the fluorescence-labeled nucleotide that is incorporated by the DNA polymerase fixed to the bottom surface of the pore is excited to emit fluorescence. In the single-molecule real-time sequencing method, by measuring fluorescence emitted from the fluorescence-labeled nucleotide that is incorporated by the DNA polymerase real time, the base sequence of DNA to be analyzed can be read.

CITATION LIST

Non-Patent Literature

NPL 1: Gerald M Cherf et al., Nat. Biotechnol. 30, No. 4, p. 349-353, 2012

NPL 2: https://nanoporetech.com/resource-centre/nanopore-community-meeting-2019-technology-update

SUMMARY OF INVENTION

Technical Problem

In the method in which DNA polymerase carries out a complementary strand synthesis reaction of a template DNA strand, for example, the nanopore DNA sequencing method or the single-molecule real-time sequencing method, DNA strands that are synthesized in the complementary strand synthesis reaction are accumulated in a tank into which DNA to be analyzed is introduced. The accumulated DNA strands cause clogging of the nanopore in the nanopore DNA sequencing method or the pore in the single-molecule real-time sequencing method or inhibition of the reaction to occur, and thus the determination accuracy of the base sequence may deteriorate.

Accordingly, the present invention has been made in consideration of the above-described circumstances, and an object thereof is to provide a composition for nucleic acid analysis, a nucleic acid analyzing method, and a nucleic acid analyzer, in which, in a base sequence determination system that performs a complementary strand synthesis reaction of a template DNA strand using DNA polymerase, inhibition of the complementary strand synthesis reaction is prevented such that a base sequence can be determined with high accuracy.

Solution to Problem

The present invention that achieves the above-described object includes the following configurations.

(1) A composition for nucleic acid analysis that is used for determining a base sequence of a nucleic acid to be analyzed when a complementary strand is synthesized by DNA polymerase using the nucleic acid to be analyzed as a template, the composition including exonuclease that degrades the complementary strand synthesized by the DNA polymerase.

(2) The composition for nucleic acid analysis according to (1), including:

a nucleic acid to be analyzed;

an adapter molecule that directly or indirectly binds to at least one end portion of the nucleic acid to be analyzed; and a nucleic acid-adapter molecule complex that inhibits the degradation by the exonuclease with the adapter molecule.

(3) The composition for nucleic acid analysis according to (2), in which the adapter molecule includes a double-stranded nucleic acid region that includes one end portion directly or indirectly binding to the nucleic acid to be analyzed and consists of base sequences complementary to each other, a pair of single-stranded nucleic acid regions that are linked to another end portion of the double-stranded nucleic acid region different from the one end portion and consist of base sequences non-complementary to each other, and a degradation inhibition portion that is provided on one of the pair of single-stranded nucleic acid regions and inhibits the nucleic acid degradation reaction by the exonuclease.

(4) The composition for nucleic acid analysis according to (3), in which among the pair of single-stranded nucleic acid regions, a single-stranded nucleic acid region having an end portion of 3'terminal includes a molecular motor binding portion to which DNA polymerase is bindable.

(5) The composition for nucleic acid analysis according to (4), in which the single-stranded nucleic acid region including the molecular motor binding portion includes a primer binding portion to which a primer is hybridizable further on the 3'terminal side than the molecular motor binding portion.

(6) The composition for nucleic acid analysis according to (4), in which the single-stranded nucleic acid region including the molecular motor binding portion includes a primer binding portion to which a primer is hybridizable further on the 3'terminal side than the molecular motor binding portion and includes plural sets including the molecular motor binding portions and the primer binding portions.

(7) The composition for nucleic acid analysis according to (5) or (6), in which a spacer to which the DNA polymerase is not bindable is provided between the molecular motor binding portion and the primer binding portion.

(8) The composition for nucleic acid analysis according to (3), in which among the pair of single-stranded nucleic acid regions, a single-stranded nucleic acid region having an end portion of 5'terminal includes a molecular motor detachment induction portion where a binding force to DNA polymerase is lower than a binding force to a nucleic acid.

(9) The composition for nucleic acid analysis according to (8), in which the molecular motor detachment induction portion is a carbon chain not including a phosphodiester bond or an abasic sequence portion.

(10) The composition for nucleic acid analysis according to (1), further including the DNA polymerase.

(11) A nucleic acid analyzing method including:

a step of synthesizing a complementary strand of a nucleic acid to be analyzed by DNA polymerase in a solution including the nucleic acid to be analyzed, DNA polymerase, nucleotide as a substrate of DNA polymerase, and exonuclease and determining a sequence of one base in response to the synthesis of one base by the DNA polymerase; and a step of degrading the single-stranded complementary strand synthesized by DNA polymerase with exonuclease.

(12) The nucleic acid analyzing method according to (11), in which in the sequence determination step, the DNA polymerase synthesizes the complementary strand of the nucleic acid to be analyzed in a first liquid tank among the first liquid tank and a second liquid tank that face each other with a membrane having a nanopore interposed therebetween such that the nucleic acid to be analyzed is moved in a direction from the second liquid tank to the first liquid tank through the nanopore to measure a signal generated during the movement of the nucleic acid to be analyzed, and in the degradation step, the nucleic acid to be analyzed for which the complementary strand is formed is moved in a direction from the first liquid tank to the second liquid tank such that the complementary strand is single-stranded and the single-stranded complementary strand is degraded by exonuclease in the first liquid tank.

(13) The nucleic acid analyzing method according to (11), in which before the sequence determination step, a step of preparing a nucleic acid-adapter molecule complex where an adapter molecule directly or indirectly binds to at least one end portion of the nucleic acid to be analyzed is provided such that degradation of the nucleic acid to be analyzed by the exonuclease is inhibited by the adapter molecule.

(14) The nucleic acid analyzing method according to (13), in which the adapter molecule includes a double-stranded nucleic acid region that includes one end portion directly or indirectly binding to the nucleic acid to be analyzed and consists of base sequences complementary to each other, a pair of single-stranded nucleic acid regions that are linked to another end portion of the double-stranded nucleic acid region different from the one end portion and consist of base sequences non-complementary to each other, and a degradation inhibition portion that is provided on one of the pair of single-stranded nucleic acid regions and inhibits the nucleic acid degradation reaction by the exonuclease, and among the pair of single-stranded nucleic acid regions, a single-stranded nucleic acid region where the degradation inhibition portion is not provided is introduced into the second liquid tank through the nanopore.

(15) The nucleic acid analyzing method according to (14), in which among the pair of single-stranded nucleic acid regions, a single-stranded nucleic acid region having an end portion of 3'terminal includes a molecular motor binding portion to which DNA polymerase is bindable, and the DNA polymerase binding to the molecular motor binding portion synthesizes the complementary strand.

(16) The nucleic acid analyzing method according to (15), in which the single-stranded nucleic acid region including the molecular motor binding portion includes a primer binding portion to which a primer is hybridizable further on the 3'terminal side than the molecular motor binding portion, and the DNA polymerase binding to the molecular motor binding portion synthesizes the complementary strand from the primer hybridized to the primer binding portion.

(17) The nucleic acid analyzing method according to (13), in which the single-stranded nucleic acid region including the molecular motor binding portion includes plural sets including the molecular motor binding portions and primer binding portions to which a primer is hybridizable further on the 3'terminal side than the molecular motor binding portion, and by repeating an operation in which a DNA polymerase closest to the nanopore among DNA polymerases binding to the molecular motor binding portion synthesizes the complementary strand from the primer hybridized to the primer binding portion such that the nucleic acid-adapter molecule complex is moved from the second liquid tank to the first liquid tank, subsequently the nucleic acid-adapter molecule complex including the complementary strand is moved from the first liquid tank to the second liquid tank to peel off the complementary strand, and the DNA polymerase closest to the nanopore synthesizes the complementary strand again such that the nucleic acid-adapter molecule complex is moved from the second liquid tank to the first liquid tank, the endonuclease degrades the peeled complementary strand in the first liquid tank.

(18) The nucleic acid analyzing method according to (16) or (17), in which a spacer to which the DNA polymerase is not bindable is provided between the molecular motor binding portion and the primer binding portion.

(19) The nucleic acid analyzing method according to (13), in which among the pair of single-stranded nucleic acid regions, a single-stranded nucleic acid region having an end portion of 5'terminal includes a molecular motor detachment induction portion where a binding force to DNA polymerase is lower than a binding force to a nucleic acid, and the DNA polymerase synthesizes the complementary strand from the primer hybridized to the primer binding portion such that the nucleic acid-adapter molecule complex is moved from the second liquid tank to the first liquid tank and the DNA polymerase is separated in the molecular motor detachment induction portion of the nucleic acid-adapter molecule complex.

(20) The nucleic acid analyzing method according to (19), in which the molecular motor detachment induction portion is a carbon chain not including a phosphodiester bond or an abasic sequence portion.

(21) A nucleic acid analyzer including:

a liquid tank that is filled with a solution including a nucleic acid to be analyzed, DNA polymerase, nucleotide as a substrate of DNA polymerase, and exonuclease and in which a complementary strand of the nucleic acid to be analyzed is synthesized by the DNA polymerase; and a detection unit that determines a sequence of one base in response to the synthesis of one base by the DNA polymerase.

(22) The nucleic acid analyzer according to (21), in which the liquid tank consists of a first liquid tank and a second liquid tank that face each other with a membrane having a nanopore interposed therebetween, and the DNA polymerase synthesizes the complementary strand of the nucleic acid to be analyzed in the first liquid tank such that the nucleic acid to be analyzed is moved in a direction from the second liquid tank to the first liquid tank through the nanopore to allow the detection unit to measure a signal generated during the movement of the nucleic acid to be analyzed.

(23) The nucleic acid analyzer according to (22) further including:

a voltage source that applies a voltage between the first liquid tank and the second liquid tank; and a control device that controls the voltage source to form a desired potential gradient between the first liquid tank and the second liquid tank.

Advantageous Effects of Invention

In the composition for nucleic acid analysis, the nucleic acid analyzing method, and the nucleic acid analyzer according to the present invention, when the complementary strand of the nucleic acid to be analyzed that is synthesized by the DNA polymerase is single-stranded, the complementary strand can be degraded by exonuclease, and the inhibition or the like of the complementary strand synthesis reaction by the DNA polymerase caused by the single-stranded complementary strand synthesized by the DNA polymerase can be prevented. Accordingly, in the composition for nucleic acid analysis, the nucleic acid analyzing method, and the nucleic acid analyzer according to the present invention, the base sequence of the nucleic acid to be analyzed can be analyzed with higher accuracy.

BRIEF DESCRIPTION OF DRAWINGS

FIG. 9F is a configuration diagram showing the step of analyzing the nucleic acid using the adapter molecule shown in FIG. 7 after the step shown in FIG. 9E.

FIG. 9G is a configuration diagram showing the step of analyzing the nucleic acid using the adapter molecule shown in FIG. 7 after the step shown in FIG. 9F.

DESCRIPTION OF EMBODIMENTS

Hereinafter, a composition for nucleic acid analysis, a nucleic acid analyzing method, and a nucleic acid analyzer according to the present invention will be described in detail with reference to the drawings. The drawings show a specific embodiment based on the principle of the present invention to understand the present invention and are not used to limit the present invention.

As the nucleic acid analyzer described in the following embodiment, a well-known biomolecular analysis device in the pertinent filed that is used for biomolecular analysis in a so-called blocking current method can be applied. Examples of the well-known biomolecular analysis device in the related art include devices disclosed in U.S. Pat. No. 5,795,782A, "Scientific Reports 4, 5000, 2014, Akahori, et al.", "Nanotechnology 25(27):275501, 2014, Yanagi et al.", "Scientific Reports, 5, 14656, 2015, Goto et al.", and "Scientific Reports 5, 16640, 2015".

In addition, the composition for nucleic acid analysis, the nucleic acid analyzing method, and the nucleic acid analyzer according to the present invention is not limited to the above-described biomolecular analysis device that is a so-called nanopore DNA sequencing device, and can also be applied to nucleic acid analysis where a single-stranded complementary strand is formed, for example, a single-molecule real-time sequencing method, the nucleic acid analysis being a method in which a complementary strand of a nucleic acid to be analyzed is synthesized by DNA polymerase to determine a sequence of one base in response to the synthesis of one base by the DNA polymerase.

First Embodiment

Figure 1:
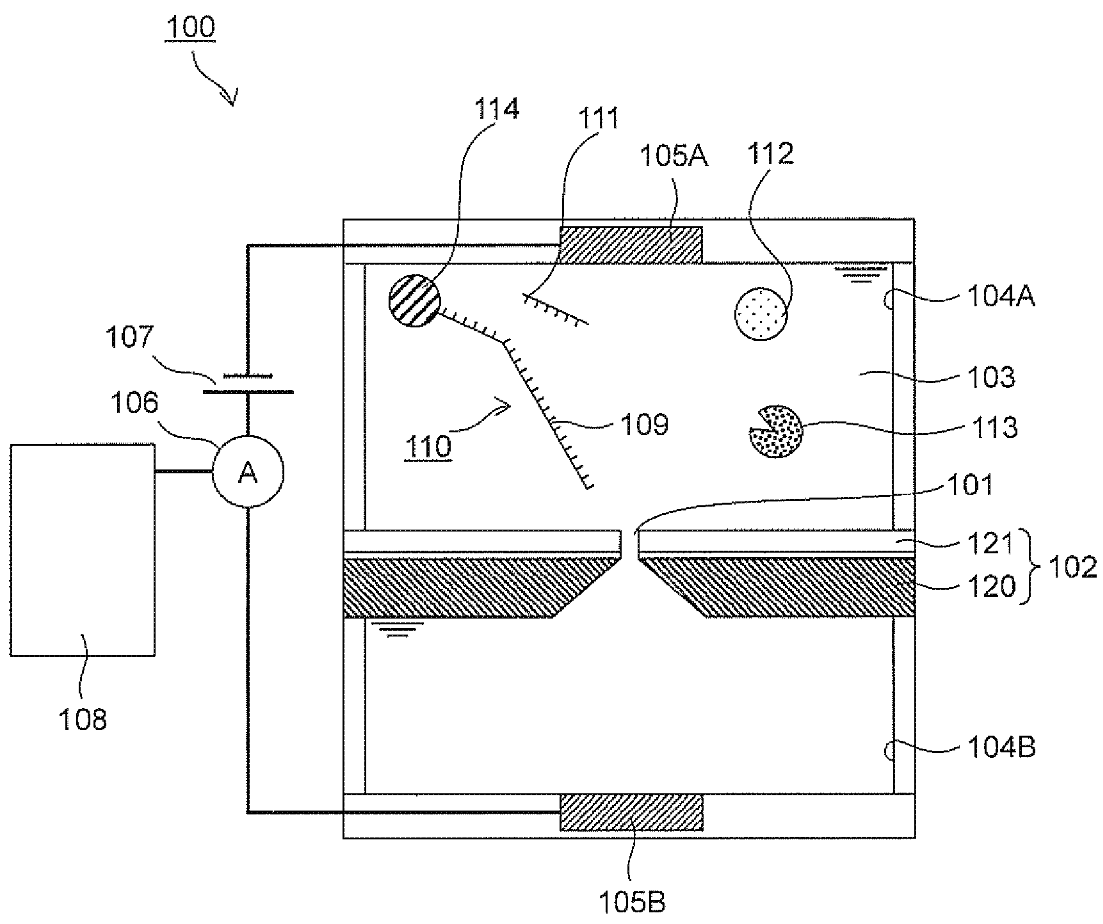
FIG. 1 is a configuration diagram schematically showing a nucleic acid analyzer to which the present invention is applied.

FIG. 1 shows a configuration example of a nucleic acid analyzer 100 that analyzes the base sequence of a nucleic acid to be analyzed. The nucleic acid analyzer 100 shown in FIG. 1 is a device for biomolecular analysis that measures an ionic current in a blocking current method, and includes: a substrate 102 where a nanopore 101 is formed; a pair of liquid tanks 104 (a first liquid tank 104A and a second liquid tank 104B) that are disposed in contact with the substrate 102 with the substrate 102 interposed therebetween and are filled with an electrolytic solution 103; and a pair of electrodes 105 (a first electrode 105A and a second electrode 105B) that are in contact with the first liquid tank 104A and the second liquid tank 104B, respectively. During the measurement, a predetermined voltage is applied between the pair of electrodes 105 from a voltage source 107 such that a current flows between the pair of electrodes 105. The size of the current flowing between the electrodes 105 is measured by an ammeter 106, and the measured value is analyzed by a computer 108.

As the electrolytic solution 103, for example, KCl, NaCl, LiCl, or CsCl is used. The electrolytic solution 103 may have the same composition or different compositions in the first liquid tank 104A and the second liquid tank 104B. The first liquid tank 104A is filled with the electrolytic solution 103 including a nucleic acid-adapter molecule complex and the like described below in detail. In addition, in the electrolytic solution 103 in the first liquid tank 104A and the second liquid tank 104B, a buffer can also be mixed to stabilize a biomolecule. As the buffer, for example, Tris, EDTA, or PBS is used. The first electrode 105A and the second electrode 105B can be prepared from a conductive material such as Ag, AgCl, or Pt.

The electrolytic solution 103 filled in the first liquid tank 104A includes a nucleic acid molecule 110 that includes a nucleic acid 109 to be analyzed, a primer 111 for amplifying the nucleic acid 109 to be analyzed, DNA polymerase 112, nucleotide (not shown) as a substrate of the DNA polymerase 112, and exonuclease 113. The nucleic acid molecule 110 includes a degradation inhibition portion 114 that is provided at 3'terminal of the nucleic acid 109 to be analyzed and inhibits degradation by the exonuclease 113.

Here, the DNA polymerase 112 refers to both of DNA-dependent DNA polymerase where DNA is a template and RNA-dependent DNA polymerase where RNA is a template. The RNA-dependent DNA polymerase is also called a reverse transcriptase. When the nucleic acid 109 to be analyzed is DNA, DNA-dependent DNA polymerase is used as the DNA polymerase 112. When the nucleic acid 109 to be analyzed is RNA, RNA-dependent DNA polymerase (reverse transcriptase) is used as the DNA polymerase 112.

The exonuclease 113 refers to an enzyme having an activity of degrading a nucleic acid fragment from 3'terminal or 5'terminal of the nucleic acid fragment. The activity of degrading 3'terminal will also be called the 3'→5'exonuclease activity or the 3'exonuclease activity. In addition, the activity of degrading 5'terminal will also be called the 5'→3'exonuclease activity or the 5'exonuclease activity.

In addition, the exonuclease 113 refers to both of ribonuclease that degrades RNA and deoxyribonuclease that degrades DNA. In particular, it is preferable that the exonuclease 113 is deoxyribonuclease. Some deoxyribonuclease also has ribonuclease activity that degrades RNA.

Specific examples of the exonuclease 113 include Exonuclease I, Exonuclease III, Exonuclease T, Exonuclease VII, Lambda Exonuclease, RecJ Exonuclease, RecBCD Nuclease, and T5 Exonuclease. Exonuclease I has the 3'-5'exonuclease activity and has a characteristic in which single-stranded DNA is specifically degraded. Exonuclease T has the 3'→5'exonuclease activity and has a characteristic in which single-stranded DNA and RNA are specifically degraded. Exonuclease VII has the 3'→5'exonuclease activity and the 5'→3'exonuclease activity and has a characteristic in which single-stranded DNA is specifically degraded. T5 Exonuclease has the 5'→3'exonuclease activity and has a characteristic in which single-stranded DNA and double-stranded DNA are specifically degraded, DNA is degraded from the nick, and the supercoil is not degraded. RecJ Exonuclease has the 5'→3'exonuclease activity and has a characteristic in which single-stranded DNA is specifically degraded, the activity depends on $Mg^{2+}$, and RecJ Exonuclease is inactivated at 65° C. for 20 minutes.

As the exonuclease 113, nucleases that do not have the degradation activity from the nick and are not inactivated under conditions of 65° C. and 20 minutes, for example, one or more nucleases selected from the group consisting of Exonuclease I, Exonuclease T, and Exonuclease VII are preferably used.

The degradation inhibition portion 114 has a function of completely inhibiting or delaying the progress of the degradation reaction by the exonuclease 113. Examples of the degradation inhibition portion 114 include a nucleic acid region that consists of a predetermined base sequence and where a steric structure capable of inhibiting degradation by exonuclease is formed and a material that binds to 3'terminal of the nucleic acid 109. For example, when an enzyme that has the 3'→5'exonuclease activity and specifically degrades single-stranded DNA is used as the exonuclease 113, the degradation of the nucleic acid molecule 110 including the nucleic acid 109 can be inhibited by binding a material to the 3'terminal of the nucleic acid 109 or by forming a steric structure.

In particular, it is preferable that the degradation inhibition portion 114 has a sufficiently larger size than the size (diameter) of the nanopore 101. By using a material having a sufficiently larger size than the size (diameter) of the nanopore 101 as the degradation inhibition portion 114, the nucleic acid 109 linked to the degradation inhibition portion 114 can be prevented from moving to the second liquid tank 104B through the nanopore 101. For example, the size of the degradation inhibition portion 114 relative to the diameter of the nanopore 101 only needs to be the size where the progress of the nucleic acid 109 can be prevented, and is desirably, for example, about 1.2 to 50 times. More specifically, when single-stranded DNA is measured as the nucleic acid 109, the diameter thereof is about 1.5 nm. Therefore, when the diameter of the nanopore 101 is about 1.5 nm to 2.5 nm, streptavidin (the diameter is about 5 nm) can be used as the degradation inhibition portion 114. When streptavidin binds to a terminal, biotin binds to the terminal. For the biotinylation of the terminal, a commercially available kit can be used. In addition, streptavidin is not particularly limited and may be, for example, modified streptavidin where modification is introduced such that the number of binding sites to biotin is one. As the degradation inhibition portion 114 other than streptavidin, for example, a complex of an anti-DIG antibody to avidin or digoxigein (DIG) and beads can be used.

In addition, examples of the degradation inhibition portion 114 include a hydrophobic molecule such as peptide, sugar chain, or cholesterol and polymer polyethylene glycol. Examples of a method of adding the material include a method of adding a reactive functional group for binding another compound, for example, amination, thiolation, or alkylation on the terminal of the nucleic acid 109.

Further, when the steric structure of the nucleic acid is used as the degradation inhibition portion 114, the steric structure is not particularly limited, and examples thereof include a hairpin structure, a guanine quadruplex (G-quadruplex, G4, or G quartet) structure (for example, a telomere structure), a DNA nanoball structure, and a DNA origami structure. In addition, the steric structure may be a structure capable of forming a hybridization or chelate structure in one molecule. Further, a measurement voltage is applied to the steric structure in the vicinity of the nanopore 101. Therefore, it is preferable that a withstand voltage at which the steric structure is maintained is the measurement voltage or higher. In this case, even when the withstand voltage at which the steric structure is maintained is lower than the measurement voltage, the withstand voltage can also be strengthened by binding to protein or the like.

Further, examples of the degradation inhibition portion 114 include a chemical modification that improves nuclease resistance. Examples of the chemical modification include a chemical modification on nucleotide and a chemical modification on a phosphodiester binding portion. For example, nuclease resistance can be improved by a chemical modification of methylation of the 2-position of nucleotide (2'-

OMe treatment (H. Inoue et al., Nucleic Acids Research 15 6131-6148 (1987)) or a chemical modification using a bridged nucleic acid (a bridged nucleic acid (BNA), a locked nucleic acid (LNA), or a 2'-0,4'-C-ethylene-bridged nucleic acids (ENA)), or a chemical modification of methylcarbamoyl ethylation. Further, examples of the chemical modification of phosphate moiety in the phosphodiester bond include phosphorothioate modification (S-modification) in which an oxygen atom is substituted with a sulfur atom. Nuclease resistance can be improved by performing the S-modification on the phosphodiester binding portion.

Further, the degradation inhibition portion 114 may directly bind to the 3'terminal of the nucleic acid 109 to be analyzed but may indirectly bind thereto. Examples of a method of binding the degradation inhibition portion 114 to the 3'terminal of the nucleic acid 109 to be analyzed include a method of using the adapter molecule including the degradation inhibition portion 114. When the nucleic acid 109 to be analyzed is double-stranded, an end portion of the adapter molecule linked to the nucleic acid 109 can be made to be a double-stranded region. By linking the adapter molecule to double-stranded nucleic acid DNA to be analyzed and subsequently modifying the adapter molecule to be single-stranded, the nucleic acid molecule 110 including the degradation inhibition portion 114 at an end portion can be prepared. When the nucleic acid 109 to be analyzed is a double-stranded DNA fragment, the adapter molecule binds to the 3'terminal with respect to one chain of the double-stranded DNA fragment.

In the double-stranded region of the adapter molecule, it is preferable that the end portion linked to the nucleic acid 109 to be analyzed is a 3'protruding end (for example, a dA protruding end). By making the end portion to be 3'dA protruding end, when the adapter molecule and the nucleic acid 109 to be analyzed are linked to each other, the formation of a homodimer of the adapter molecule can be prevented.

The adapter molecule and the nucleic acid 109 may be indirectly linked to each other. The indirect linking refers to both of linking between the adapter molecule and the nucleic acid 109 through a nucleic acid fragment having a predetermined number of bases and linking between the adapter molecule and the nucleic acid 109 through a functional group that is introduced depending on the kind of the nucleic acid 109.

In addition, the length and the base sequence of the adapter molecule are not particularly limited, and any length and any base sequence can be adopted. For example, the length of the adapter molecule can be 5 to 100 bases, 10 to 80 bases, 15 to 60 bases, or 20 to 40 bases. In particular, in the base sequence of the adapter molecule, it is preferable that the 3'terminal side consists of a sequence complementary to the primer 111 and the 5'terminal side consists of a sequence to which DNA polymerase is bindable.

The primer 111 can be designed to be hybridized to the adapter molecule. In this case, when the adapter molecule is not used, the primer 111 can be designed to be hybridized to a predetermined position of the nucleic acid molecule 110. Here, the primer 111 is not particularly limited and can be single-stranded nucleotide having, for example, 5 to 40 bases, preferably 15 to 35 bases, and more preferably 18 to 25 bases.

On the other hand, the substrate 102 of the nucleic acid analyzer shown in FIG. 1 includes a base 120 and a membrane 121 that is formed on one main surface of the base 120. The nanopore 101 is formed in the membrane 121. In addition, the substrate 102 may include an insulating layer (not shown). The base 120 can be formed of an electrical insulator material, for example, an inorganic material or an organic material (including a polymer material). Examples of the electrical insulator material forming the base 120 include silicon, a silicon compound, glass, quartz, polydimethylsiloxane (PDMS), polytetrafluoroethylene (PTFE), polystyrene, and polypropylene. Examples of the silicon compound include silicon nitride, silicon oxide, silicon carbide, and silicon oxynitride. In addition, the base 120 can be prepared from any of the materials and may be, for example, silicon, or the silicon compound. The nanopore 101 may be a lipid bilayer (biopore) formed of an amphiphilic molecular layer in which protein having a pore at the center is embedded.

The size and the thickness of the substrate 102 are not particularly limited as long as the nanopore 101 can be provided. The substrate 102 can be prepared using a well-known method in the pertinent technical field or can also be available as a commercially available product. For example, the substrate 102 can be prepared using photolithography, electron beam lithography, etching, laser ablation, injection molding, casting, molecular beam epitaxy, chemical vapor deposition (CVD), dielectric breakdown, or a technique using an electron beam or a focused ion beam. The substrate 102 may be coated to avoid adsorption of a non-target molecule on the surface.

The substrate 102 includes at least one nanopore 101. Specifically, the nanopore 101 is provided on the membrane 121. In some cases, the nanopore 101 may be provided on the membrane 121 and the base 120. Here, "nanopore" and "pore" refer to a through-hole having a diameter of a nanometer (nm) size (that is, 1 nm or more and less than 1 μm) that penetrates the substrate 102 and communicates with the first liquid tank 104A and the second liquid tank 104B.

It is preferable that the substrate 102 has the membrane 121 for providing the nanopore 101. That is, by forming the membrane 121 on the substrate 120 with a material and a thickness suitable for forming a nano-sized pore, the nanopore 101 can be provided on the substrate 102 simply and efficiently. From the viewpoint of easiness of the formation of the nanopore 101, the material of the membrane 121 is preferably, for example, silicon oxide ($SiO_2$), silicon nitride (SiN), silicon oxynitride (SiON), a metal oxide, a metal silicate, molybdenum disulfide ($MoS_2$), or graphene. The thickness of the membrane 121 is 1 Å (angstrom) to 200 nm, preferably 1 Å to 100 nm, and more preferably 1 Å to 50 nm, and, for example, is about 5 nm. In addition, the membrane 121 (and the entire substrate 102 in some cases) may be substantially transparent. Here, "substantially transparent" represents that transmission of about 50% or more and preferably 80% or more of external light is allowed. In addition, the membrane may be a monolayer or a multilayer.

It is also preferable that an insulating layer is provided on the membrane 121. The thickness of the insulating layer is preferably 5 nm to 50 nm. For the insulating layer, any insulator material can be used. For example, silicon or a silicon compound (for example, silicon nitride or silicon oxide) is preferably used.

As the size of the nanopore 101, an appropriate size can be selected depending on the type of a biopolymer to be analyzed. The nanopore may have a uniform diameter or may have different diameters depending on sites. In the nanopore provided in the membrane 121 of the substrate 102, the minimum diameter, that is, the smallest diameter of the nanopore 101 is 100 nm or less, for example, 0.9 nm to 100 nm, preferably 0.9 nm to 50 nm, for example, 0.9 nm to 10 nm. Specifically, the minimum diameter is 1 nm or more and 5 nm or less, for example, preferably 3 nm or more and 5 nm or less. The nanopore 101 may also communicate with a pore having a diameter of 1 μm or more formed in the base 120.

In addition, when a biomolecule to be analyzed is a single-stranded nucleic acid (DNA), the diameter of the single-stranded DNA is about 1.4 nm. Therefore, the diameter of the nanopore 101 is preferably about 1.4 nm to 10 nm, more preferably about 1.4 nm to 2.5 nm, and specifically about 1.6 nm. When a biomolecule to be analyzed is a double-stranded nucleic acid (DNA), the diameter of the double-stranded DNA is about 2.6 nm. Therefore, the diameter of the nanopore 101 is preferably about 3 nm to 10 nm and more preferably about 3 nm to 5 nm.

The depth (length) of the nanopore 101 can be adjusted by adjusting the total thickness of the membrane 121 or the substrate 102. It is preferable that the depth of the nanopore 101 is aligned to the length of a monomer unit forming the biomolecule to be analyzed. For example, when a nucleic acid is selected as the biomolecule to be analyzed, the depth of the nanopore 101 is preferably the size of about one base, for example, about 0.3 nm. On the other hand, the depth of the nanopore can be 2 times or more, 3 times or more, or 5 times or more the size of a monomer unit forming the biomolecule. For example, in a case where the biomolecule is formed of a nucleic acid, even when the depth of the nanopore is the size of three bases or more, for example, about 1 nm or more, the biomolecule can be analyzed. As a result, high-accuracy analysis can be performed while maintaining the robustness of the nanopore. In addition, the shape of the nanopore is basically a circular shape and can also be an elliptical shape or a polygonal shape.

Further, at least one nanopore 101 can be provided in the substrate 102. When a plurality of nanopores 101 are provided, the nanopores 101 may be arranged regularly or randomly. The nanopore 101 can be formed using a nano lithography technique, an ion beam lithography technique, or the like by being irradiated with, for example, an electron beam of a transmission electron microscope (TEM) using a well-known method in the pertinent technical field.

The device shown in FIG. 1 includes one nanopore 101 provided between the pair of liquid tanks 104A and 104B. However, this configuration is merely exemplary, and a configuration in which a plurality of nanopores 101 are provided between the pair of liquid tanks 104A and 104B can also be adopted. In addition, in another example, an array device can also be used in which a plurality of nanopores 101 are formed in the substrate 102 and the respective regions between the plurality of nanopores 101 are separated by a partition wall. In the array device, a common tank can be used as the first liquid tank 104A, and a plurality of individual tanks can be used as the second liquid tank 104B. In this case, an electrode can be disposed in each of the common tank and the individual tanks.

In the array type device configuration where a plurality of membranes having a nanopore are provided, it is preferable that the membranes having a nanopore are arranged regularly. An interval at which the plurality of membranes are disposed can be determined depending on the electrode to be used and the capacity of an electrical measurement system and is 0.1 μm to 10 μm and preferably 0.5 μm to 4 μm.

A method of forming the nanopore in the membrane is not particularly limited. For example, electron beam irradiation by an transmission electron microscope or the like or dielectric breakdown by voltage application can be used. For example, a method described in "Itaru Yanagi et al., Sci. Rep. 4, 5000(2014)" can be used.

On the other hand, the first electrode 105A and the second electrode 105B are not particularly limited and can be prepared from, for example, a platinum group such as platinum, palladium, rhodium, or ruthenium, gold, silver, copper, aluminum, nickel, or the like, graphite such as graphene (which is any one of a monolayer or a multilayer), tungsten, or tantalum.

Figure 2:
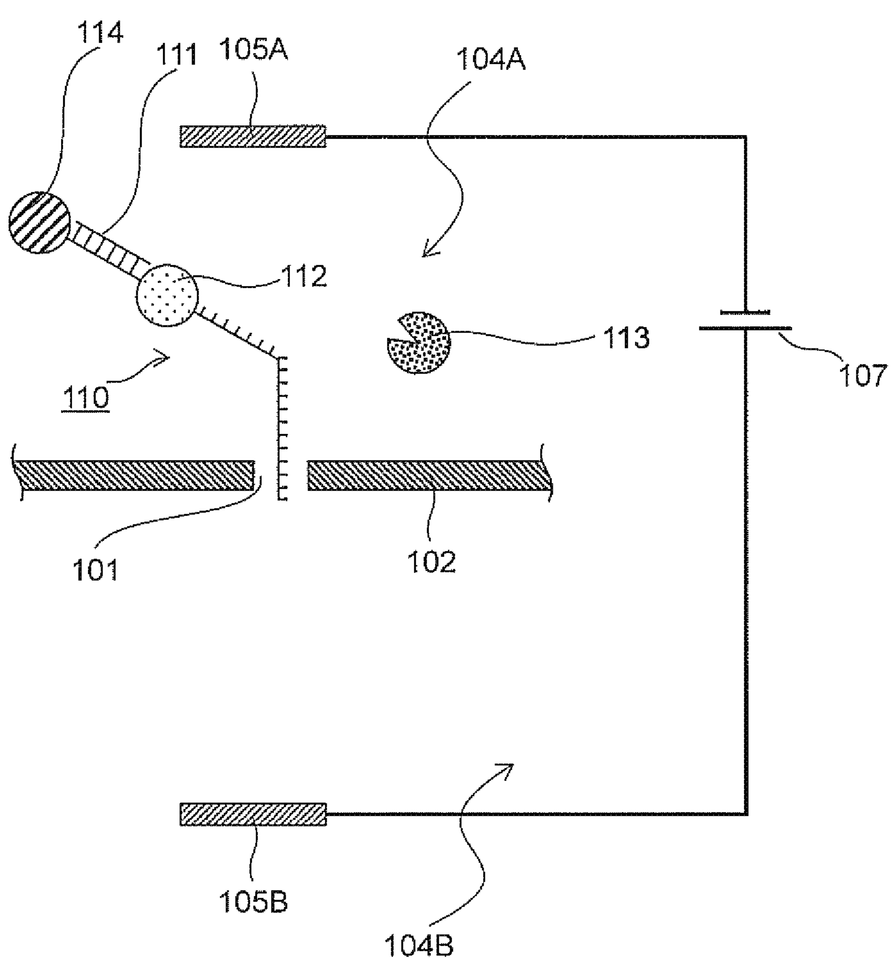
FIG. 2 is a configuration diagram schematically showing a step of analyzing a nucleic acid to be analyzed using a composition for nucleic acid analysis to which the present invention is applied.
Figure 3:
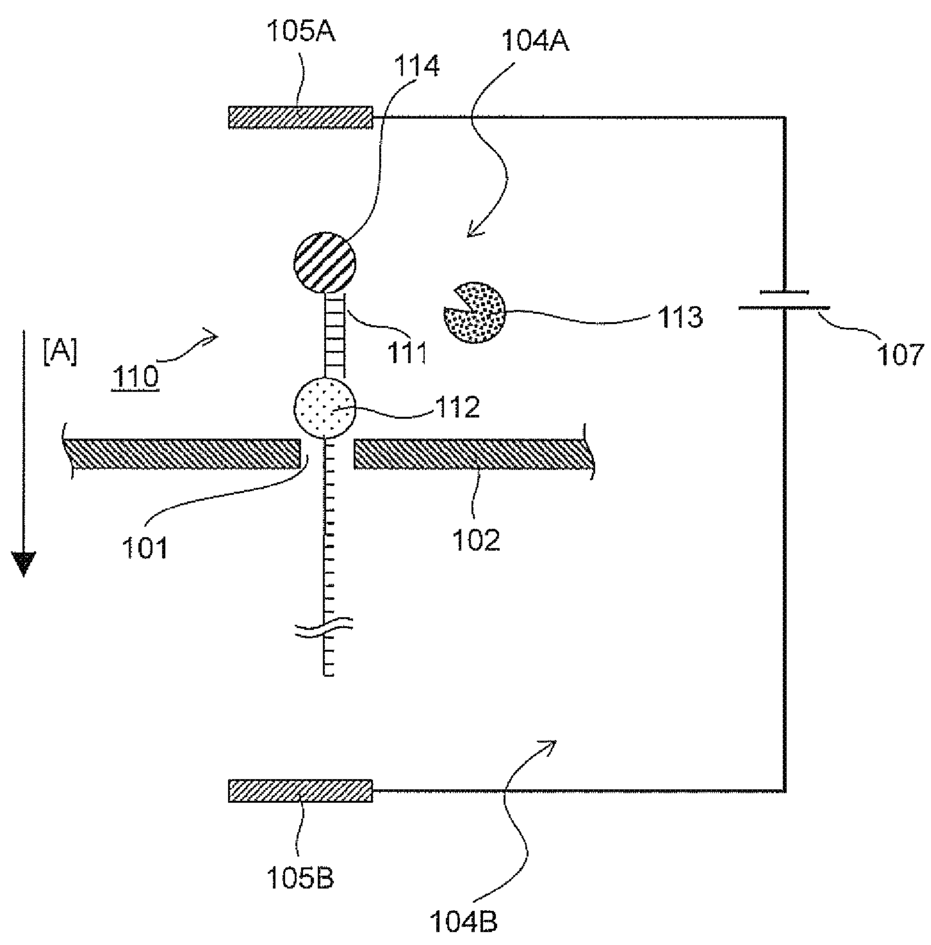
FIG. 3 is a configuration diagram schematically showing a step of analyzing the nucleic acid to be analyzed after the step shown in FIG. 2.

In the nucleic acid analyzer having the above-described configuration, in a state where the first liquid tank 104A is filled with the electrolytic solution 103 including the nucleic acid molecule 110 that includes the nucleic acid 109 to be analyzed, the primer 111, the DNA polymerase 112, the nucleotide (not shown) as the substrate of the DNA polymerase 112, and the exonuclease 113, when a voltage is applied between the first electrode 105A and the second electrode 105B to form a potential gradient that makes the first liquid tank 104A side to have a negative potential or a ground potential and makes the second liquid tank 104B to have a positive potential, a terminal (5'terminal) of the nucleic acid molecule 110 where the degradation inhibition portion 114 is not provided moves in a direction toward the nanopore 101 as shown in FIG. 2. As shown in FIG. 3, due to the potential gradient between the first liquid tank 104A and the second liquid tank 104B, the nucleic acid molecule 110 moves to the second liquid tank 104B through (via) the nanopore 101 (direction indicated by arrow A in FIG. 3).

In the state of FIG. 2 and the state of FIG. 3, in the electrolytic solution 103, the primer 111 is hybridized to the nucleic acid molecule 110, and the DNA polymerase binds to the nucleic acid molecule 109. The nuclease 113 in the electrolytic solution 103 starts to degrade some primer 111 that is not hybridized to the nucleic acid molecule 110. By including the primer 111 at a high concentration, the primer 111 can be sufficiently hybridized to the nucleic acid molecule 110. In addition, by filling the first liquid tank 104A with the electrolytic solution 103 in a state where the primer 111 is hybridized to the nucleic acid molecule 110, the degradation of the primer 111 by the nuclease 113 can be avoided. The nucleic acid molecule 110 includes the degradation inhibition portion 114, and thus the degradation by the nuclease 113 can be avoided.

The voltage gradient formed between the first liquid tank 104A and the second liquid tank 104B only needs to make the second liquid tank 104B to have a positive potential and to make the first liquid tank 104A to have a negative potential or a ground potential such that the negatively charged nucleic acid molecule 110 moves.

In the state shown in FIG. 3, due to the voltage gradient formed between the first liquid tank 104A and the second liquid tank 104B, the nucleic acid molecule 110 moves in the direction of the arrow A, and the DNA polymerase 112 as a molecular motor arrives at the nanopore 101. Here, a dimension Dm of the DNA polymerase 112 is larger than a diameter Dn of the nanopore 101 (Dm>Dn). Therefore, when the DNA polymerase 112 arrives at an entrance (the first liquid tank 104A side) of the nanopore 101, the DNA polymerase 112 cannot pass through the nanopore 101 to advance to the exit side (the second liquid tank 104B side) and is stopped at the entrance of the nanopore 101.

Figure 4:
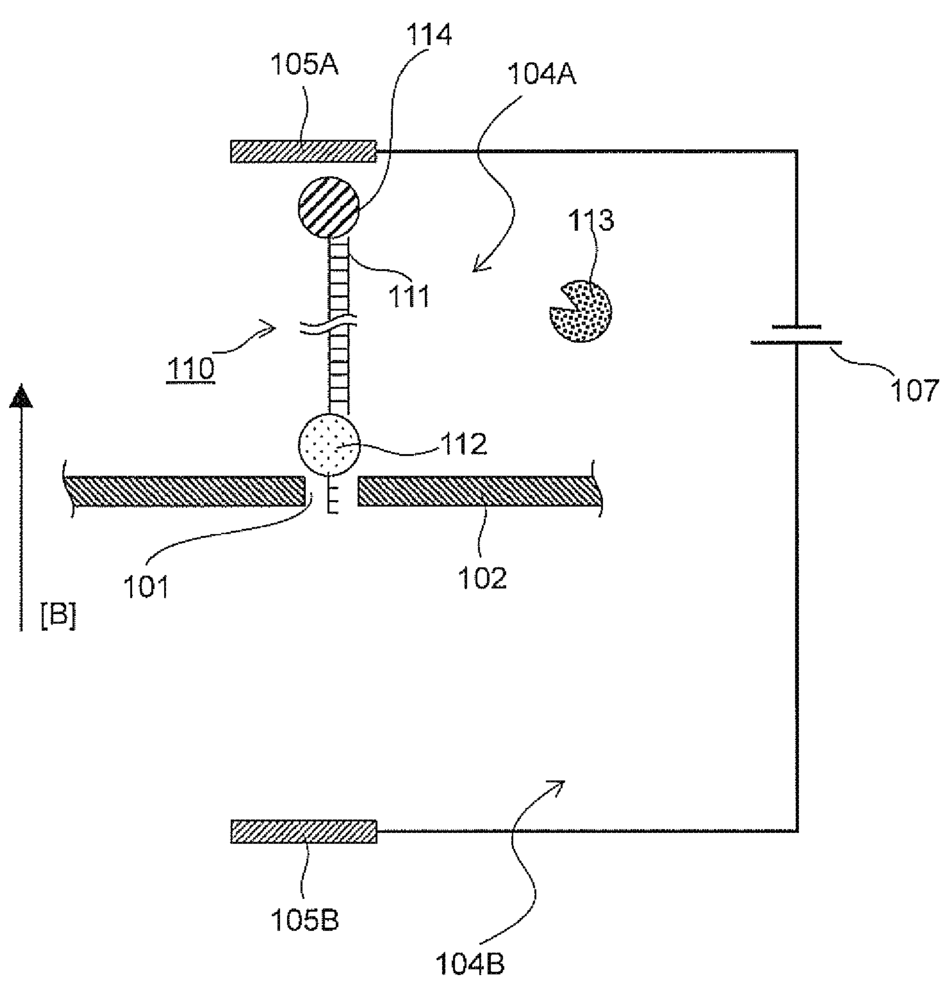
FIG. 4 is a configuration diagram schematically showing the step of analyzing the nucleic acid to be analyzed after the step shown in FIG. 3.

As shown in FIG. 4, the DNA polymerase 112 starts a complementary strand synthesis reaction from the 3'terminal of the primer 111 in a direction from the 5'terminal to the 3'terminal and synthesizes a complementary strand 115. When the complementary strand synthesis reaction by the DNA polymerase 112 progresses, a force where the nucleic acid molecule 110 is pulled by the DNA polymerase 112 is stronger than a force where the nucleic acid molecule 110 moves to the second liquid tank 104B due to the potential gradient. Therefore, the nucleic acid molecule 110 is transported against the potential gradient in a direction toward the first liquid tank 104A (direction indicated by arrow B in FIG. 4). At this time, although described below in detail, base sequence information of the nucleic acid molecule 110 that passes through the nanopore 101 can be acquired.

By controlling the transport of the nucleic acid molecule 110 using the DNA polymerase 112 as described above, the nanopore passage speed can be made to be 100 μs or faster per base, and the blocking current derived each of the bases can be sufficiently measured.

Here, a method of determining the base sequence information will be described in more detail. As the bases, four types of ATGC are present. When the bases pass through the nanopore 101, the value of ionic current (blocking current) unique to each of the types is measured. Accordingly, the ionic current during the passage through the nanopore 101 is measured in advance using a known sequence, and the current value corresponding to the known sequence is stored in a memory of the computer 108. By comparing current values measured when bases forming the nucleic acid molecule 110 sequentially pass through the nanopore 101 to the current values corresponding to the known sequence stored in the memory, the types of the bases forming the nucleic acid molecule 110 to be analyzed can be sequentially determined. Here, the known sequence for which the ionic currents are measured in advance can be the number of bases corresponding to the depth (length) of the nanopore 101 (for example, a sequence of 2 bases, a sequence of 3 bases, or a sequence of 5 bases).

In addition, in a base sequence determination method of the nucleic acid molecule 110, the nucleic acid molecule 110 may be labeled with a fluorescent substance, the fluorescent substance in the vicinity of the nanopore 101 may be excited to emit fluorescence, and the emitted fluorescence may be detected. Further, a method of determining the base sequence of the nucleic acid 109 in a hybridization base described in Reference Literature 1 (NANOLETTERS (2005), Vol. 5, pp. 421-424) can also be applied.

In the method of determining the base sequence information, the state shown in FIG. 3 transitions to the state shown in FIG. 4 due to the complementary strand synthesis reaction by the DNA polymerase 112, and when the nucleic acid molecule 110 moves from the second liquid tank 104B to the first liquid tank 104A through the nanopore 101, the base sequence information of the nucleic acid molecule 110 can be acquired. At a stage of completion of acquiring the base sequence information of the nucleic acid molecule 110, by further strengthening the voltage gradient formed between the first liquid tank 104A and the second liquid tank 104B, a force where the nucleic acid molecule 110 moves in a direction toward the second liquid tank 104B according to the potential gradient is stronger than a force where the nucleic acid molecule 110 is pulled by the DNA polymerase 112. As a result, the nucleic acid molecule 110 moves in the direction toward the second liquid tank 104B as shown in FIG. 5.

Figure 5:
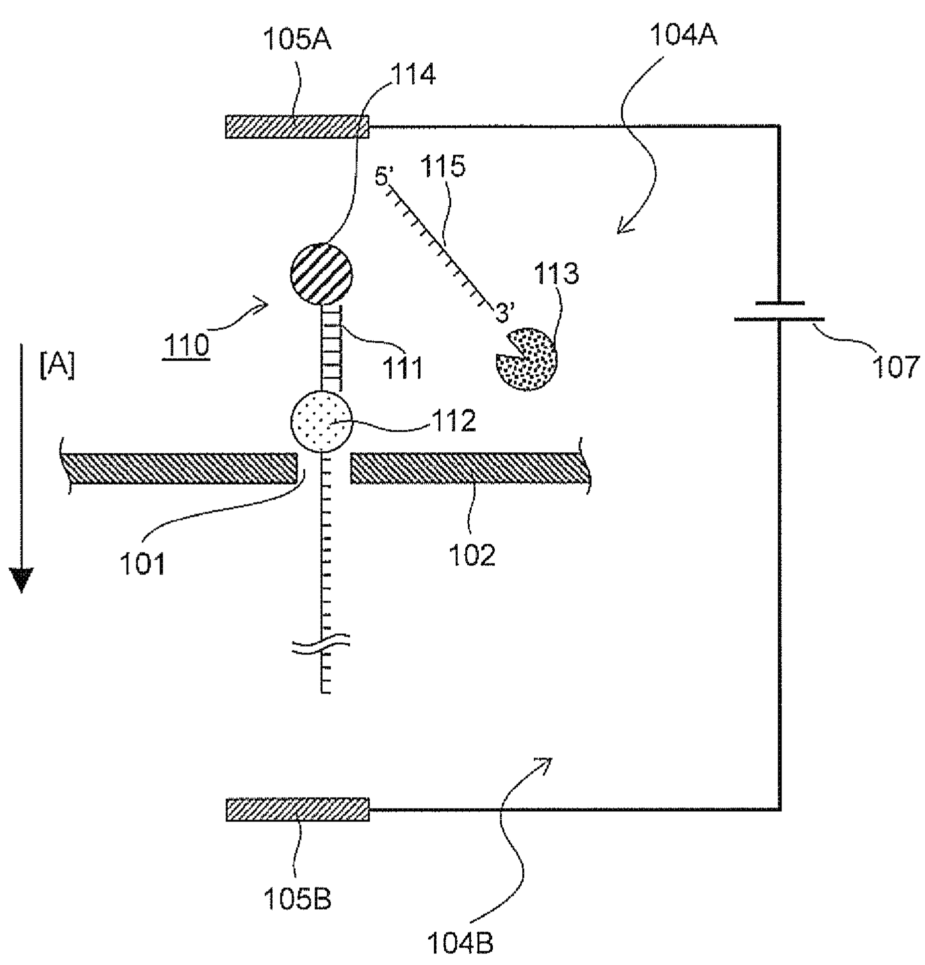
FIG. 5 is a configuration diagram schematically showing a step of analyzing the nucleic acid to be analyzed after the step shown in FIG. 4.
Figure 6:
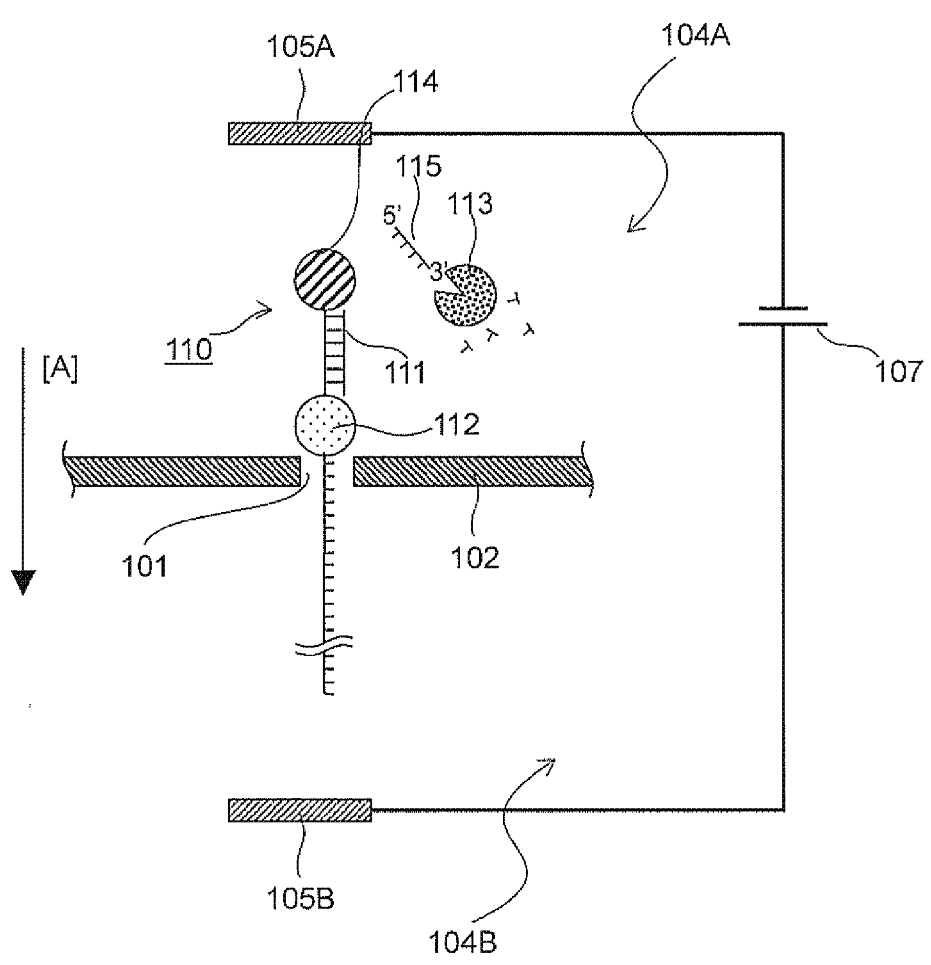
FIG. 6 is a configuration diagram schematically showing the step of analyzing the nucleic acid to be analyzed after the step shown in FIG. 5.

When the state shown in FIG. 4 transitions to the state shown in FIG. 5, the complementary strand 115 synthesized by the DNA polymerase 112 is peeled off from the nucleic acid molecule 110. In addition, the primer 111 in the electrolytic solution 103 filled in the first liquid tank 104A is hybridized again to the nucleic acid molecule 110, and the DNA polymerase 112 binds thereto again. The peeled complementary strand 115 is degraded from the 3'terminal side by the exonuclease 113 as shown in FIG. 6. In addition, in the state shown in FIGS. 5 and 6, by weakening the voltage gradient formed between the first liquid tank 104A and the second liquid tank 104B, the DNA polymerase 112 starts the complementary strand synthesis reaction again from the 3'terminal of the hybridized primer 111 in the direction from the 5'terminal to the 3'terminal and synthesizes the complementary strand 115 again. That is, a force where the nucleic acid molecule 110 is pulled by the complementary strand synthesis reaction of the DNA polymerase 112 is stronger than a force where the nucleic acid molecule 110 moves to the second liquid tank 104B side due to the electron gradient, and thus, the nucleic acid molecule 110 is transported against the potential gradient in the direction toward the first liquid tank 104A (direction indicated by arrow B in FIG. 4). At this time, the base sequence information of the nucleic acid molecule 110 that passes through the nanopore 101 can be acquired again.

As described above, the base sequence information of the nucleic acid 109 may be acquired only when the nucleic acid molecule 110 is transported in the arrow [B] direction of FIG. 4, or the base sequence information of the nucleic acid 109 may also be acquired when the nucleic acid molecule 110 moves in the arrow [A] direction of FIG. 5. During the movement in the arrow [B] direction of FIG. 4, the base sequence information is determined from the 5'terminal to the 3'terminal of the nucleic acid 109, and during the movement in the arrow [A] direction of FIG. 5, the base sequence information is determined from the 3'terminal to the 5'terminal of the nucleic acid 109. In either case, plural sets of base sequence information regarding the nucleic acid 109 can be acquired, and the accuracy of the base sequence information can be improved. In other words, by reciprocating the nucleic acid molecule 110, the base sequence of the nucleic acid 109 can be read multiple times, and the reading accuracy can be improved.

In addition, examples of a method of switching between applied voltages to transition the state shown in FIGS. 5 and 6 to the state shown in FIG. 4 include a method of automatically switching between the applied voltages at a predetermined time interval. In this case, a timing of switching between the voltages is programmed in the computer 108, and by controlling the voltage source 107 in accordance with the program, the applied voltage can be switched at the timing.

As described above, the electrolytic solution 103 filled in the first liquid tank 104A includes the endonuclease 113, and the complementary strand 115 synthesized by the DNA polymerase 112 can be degraded by the endonuclease 113 in the first liquid tank 104A. Therefore, the complementary strand 115 synthesized by the DNA polymerase 112 can be prevented from approaching the nanopore 101 and inhibiting the complementary strand synthesis reaction by the DNA polymerase 112 or from blocking the nanopore 101 and inhibiting the transport of the nucleic acid molecule 110. As a result, with the nucleic acid analyzer described above, the base sequence of the nucleic acid 109 to be analyzed can be analyzed with high accuracy.

Second Embodiment

In the embodiment, a method of analyzing the nucleic acid molecule 110 including the nucleic acid 109 to be analyzed using an adapter molecule 300 shown in FIG. 7 will be described. For the adapter molecule 300 shown in FIG. 7 and a nucleic acid analyzer using it, the same configurations as those of the nucleic acid analyzer shown in FIG. 1 and the like are represented by the same reference numerals, and the detailed description thereof will not be repeated.

Figure 7:
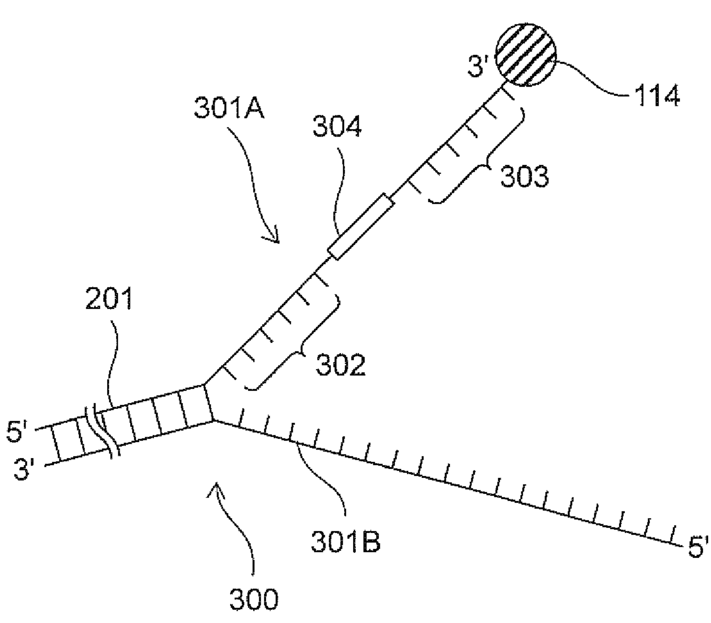
FIG. 7 is a configuration diagram schematically showing an adapter molecule used in a nucleic acid analyzing method to which the present invention is applied.

The adapter molecule 300 shown in FIG. 7 includes: a double-stranded nucleic acid region 201 that directly binds to the nucleic acid 109 (double-stranded DNA) to be analyzed; and a pair of single-stranded nucleic acid regions 301A and 301B that are linked to an end portion of the double-stranded nucleic acid region 201 different from an end portion binding to the nucleic acid 109 and consist of base sequences non-complementary to each other. The single-stranded nucleic acid region 301A includes the degradation inhibition portion 114 binding to 3'terminal, and the single-stranded nucleic acid region 301B includes 5'terminal. In the example of the adapter molecule 300 shown in FIG. 7, the exonuclease 113 that has the 3'→5'exonuclease activity and specifically degrades single-stranded DNA is used, and the degradation inhibition portion 114 is disposed at the end portion of the single-stranded nucleic acid region 301A having the 3'terminal. However, when the exonuclease 113 that has the 5'→3'exonuclease activity and specifically degrades single-stranded DNA is used, the degradation inhibition portion 114 is disposed at the end portion of the single-stranded nucleic acid region 301B having the 5'terminal instead of the end portion of the single-stranded nucleic acid region 301A.

By adding the nucleic acid 109 to be analyzed, the adapter molecule 300, and DNA ligase to the electrolytic solution 103 filled in the first liquid tank 104A, in the electrolytic solution 103 filled in the first liquid tank 104A, a nucleic acid-adapter molecule complex where the adapter molecule 300 binds to the nucleic acid 109 to be analyzed can be formed. The nucleic acid-adapter molecule complex where the adapter molecule 300 and the nucleic acid 109 to be analyzed are linked to each other by the DNA ligase may be prepared in advance and added to the electrolytic solution 103. In addition, although not shown, the adapter molecule 300 and the nucleic acid 109 may be indirectly linked to each other. The indirect linking refers to linking between the adapter molecule 300 and the nucleic acid 109 through a nucleic acid fragment having a predetermined number of bases.

Further, in the adapter molecule 300, it is preferable that the end portion of the double-stranded nucleic acid region 201 linked to the nucleic acid 109 is a 3'protruding end (for example, a dA protruding end). By making the end portion to be 3'dA protruding end, when the adapter molecule 300 and the nucleic acid 109 are linked to each other, the formation of a dimer of the adapter molecule 300 can be prevented.

Further, in the adapter molecule 300, the length and the base sequence of the double-stranded nucleic acid region 201 are not particularly limited, and any length and any base sequence can be adopted. For example, the length of the double-stranded nucleic acid region 201 can be 5 to 100 bases, 10 to 80 bases, 15 to 60 bases, or 20 to 40 bases.

Further, in the adapter molecule 300, the lengths and the base sequences of the single-stranded nucleic acid regions 301A and 301B are not particularly limited, and any length and any base sequence can be adopted. The single-stranded nucleic acid regions 301A and 301B may have the same length or may have different lengths. The single-stranded nucleic acid regions 301A and 301B may have base sequences common to each other and, if non-complementary, may have completely different base sequences. Being non-complementary represents that the proportion of the complementary sequence in the base sequences of the single-stranded nucleic acid regions 301A and 301B is 30% or less, preferably 20% or less, more preferably 10% or less, still more preferably 5% or less, and most preferably 3% or less.

The lengths of the single-stranded nucleic acid regions 301A and 301B can be, for example, 10 to 200 bases, 20 to 150 bases, 30 to 100 bases, or 50 to 80 bases. In addition, in the single-stranded nucleic acid region 301B, the base sequence (for example, 20 bases) on the 5'terminal side can be a base sequence where 90% or more of bases consist of thymine and preferably a base sequence where 100% of bases consist of thymine. By setting the proportion of thymine in the base sequence on the 5'terminal side to be in the above-described range, the formation of a high order structure can be prevented, and a shape that is likely to be introduced into the nanopore 101 can be adopted.

The single-stranded nucleic acid region 301A in the adapter molecule 300 includes a molecular motor binding portion 302 to which the DNA polymerase 112 is bindable. In addition, the single-stranded nucleic acid region 301A in the adapter molecule 300 shown in FIG. 7 includes a primer binding portion 303 where the primer 111 is hybridizable on the 3'terminal side of the molecular motor binding portion 302. The primer binding portion 303 only needs to have a sequence complementary to the base sequence of the primer to be used and is not limited to a specific base sequence. Here, the primer 111 is not particularly limited and can be single-stranded nucleotide having, for example, 5 to 40 bases, preferably 15 to 35 bases, and more preferably 18 to 25 bases. Accordingly, the primer binding portion 303 can be a region having 10 to 40 bases, preferably 15 to 35 bases, and more preferably 18 to 25 bases that is a region consisting of a base sequence complementary to the base sequence of the primer 111.

Further, the single-stranded nucleic acid region 301A in the adapter molecule 300 shown in FIG. 7 includes a spacer 304 that is provided between the molecular motor binding portion 302 and the primer binding portion 303. Here, the spacer 304 refers to a region to which the DNA polymerase 112 is not bindable, that is, a region that does not include bases consisting of AGCT. The spacer 304 is not particularly limited and can be a linear conjugate not including a base. In particular, the length of the spacer 304 is preferably a length corresponding to at least 2 bases, that is, about 0.6×2 nm or more. In other words, the molecular motor binding portion 302 and the primer binding portion 303 can be spaced by the spacer 304 by 2 bases or more (about 0.6×2 nm or more). Examples of a material forming the spacer 304 include materials that can be disposed in a DNA strand, for example, C3 Spacer, PC spacer, Spacer 9, Spacer 18, and d Spacer provided by Integrated DNA Technologies Inc. In addition, as the spacer 304, for example, a linear carbon chain, a linear amino acid, a linear fatty acid, or a linear sugar chain can be used.

Further, in the adapter molecule 300 shown in FIG. 7, a predetermined region in the double-stranded nucleic acid region 201 can be used as a tag sequence (not shown). The tag sequence is also called a barcode sequence or an index sequence and refers to a base sequence unique to the adapter molecule 300. For example, by preparing a plurality of adapter molecules 300 that are different from each other only in the tag sequence in advance, the type of the adapter molecule 300 used can be specified based on the tag sequence.

A method of analyzing the biomolecule 109 using the adapter molecule 300 having the above-described configuration will be described using FIGS. 8A and 8B and FIGS. 9A to 9G.

Figure 8A:
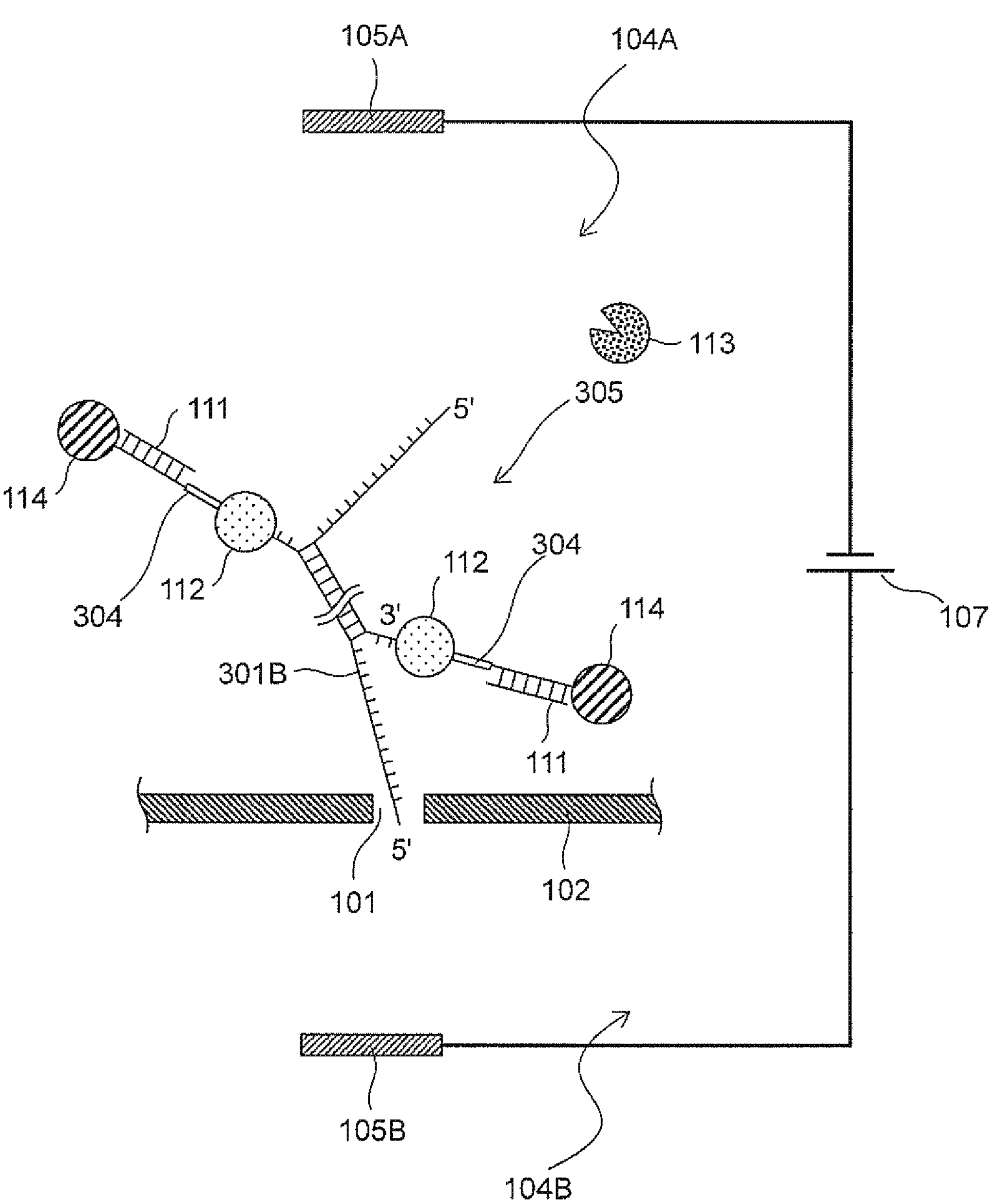
FIG. 8A is a configuration diagram showing the step of analyzing the nucleic acid using the adapter molecule shown in FIG. 7.

First, a nucleic acid-adapter molecule complex 305 where the adapter molecule 300 binds to each of opposite end portions of the nucleic acid 109 is prepared. The first liquid tank 104A is filled with the electrolytic solution including the nucleic acid-adapter molecule complex 305, the DNA polymerase 112, the primer 111, and the exonuclease 113. As a result, as shown in FIG. 8A, the DNA polymerase 112 binds to the molecular motor binding portion 302 in the adapter molecule 300, and the primer 111 is hybridized to the primer binding portion 303. The primer 111 can also be hybridized to the primer binding portion 303 of the adapter molecule 300 in advance.

Figure 8B:
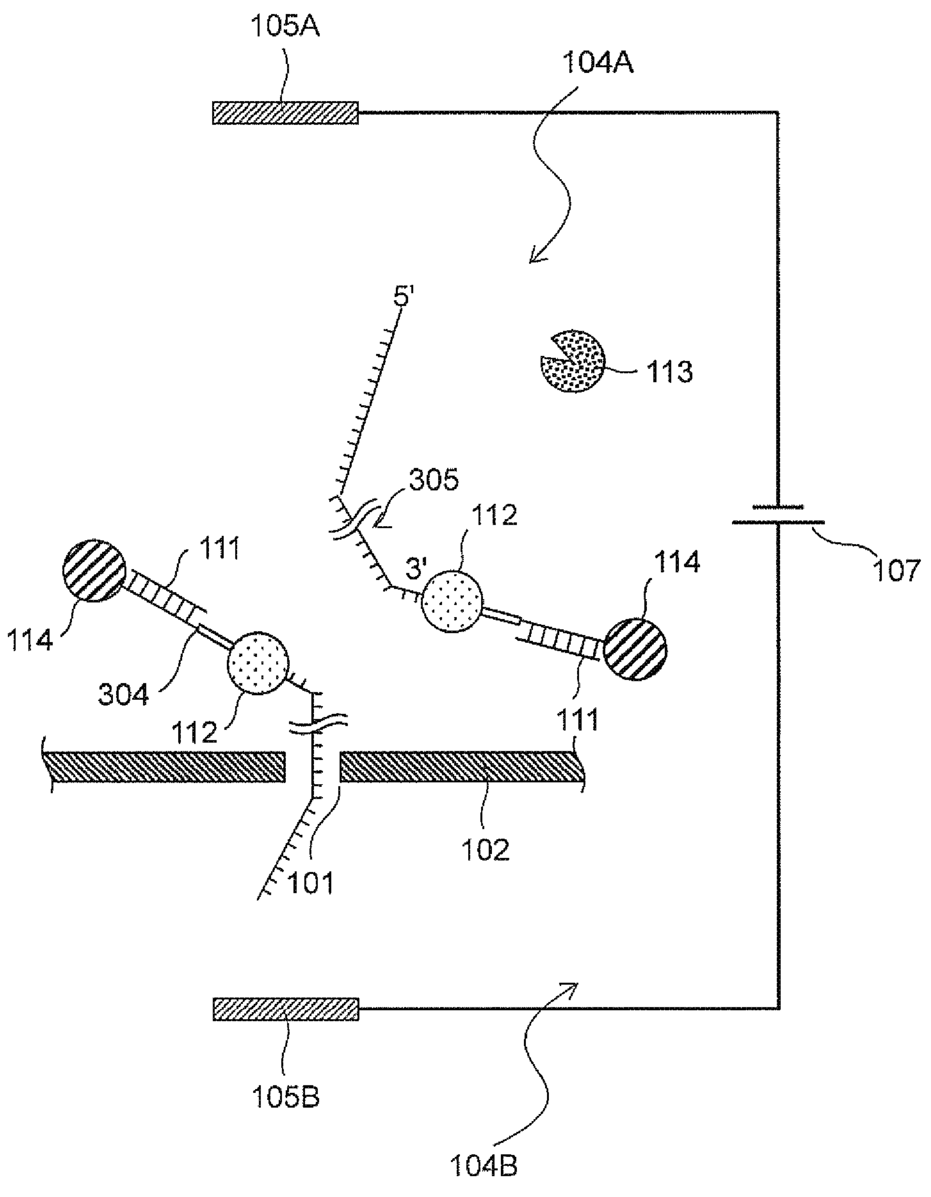
FIG. 8B is a configuration diagram showing the step of analyzing the nucleic acid using the adapter molecule shown in FIG. 7 after the step shown in FIG. 8A.

Next a voltage is applied between the first electrode 105A and the second electrode 105B to form a potential gradient that makes the first liquid tank 104A side to have a negative potential and makes the second liquid tank 104B to have a positive potential. As a result, the single-stranded nucleic acid region 301B moves in the direction toward the nanopore 101, and the 5'terminal region of the single-stranded nucleic acid region 301B is introduced into the nanopore 101. As shown in FIG. 8B, due to the potential gradient between the first liquid tank 104A and the second liquid tank 104B, the nucleic acid-adapter molecule complex 305 moves to the second liquid tank 104B through (via) the nanopore 101. At this time, the double-stranded nucleic acid (the double-stranded nucleic acid region 201 and the nucleic acid 109 in the adapter molecule 300) in the nucleic acid-adapter molecule complex 305 is peeled off (unzipped).

This way, when the adapter molecule 300 is used, a single-stranded nucleic acid that can pass through the nanopore 101 can be prepared without performing a complicated modification treatment (for example, a heat treatment) on the double-stranded nucleic acid 109. That is, when the adapter molecule 300 is used, the double-stranded nucleic acid 109 can be easily peeled off. In the state shown in FIGS. 8A and 8B, the primer 111 and the DNA polymerase 112 are spaced from each other by the length of the spacer 304. Therefore, the complementary strand synthesis reaction by the DNA polymerase 112 does not start from the 3'terminal of the primer 111.

Figure 9A:
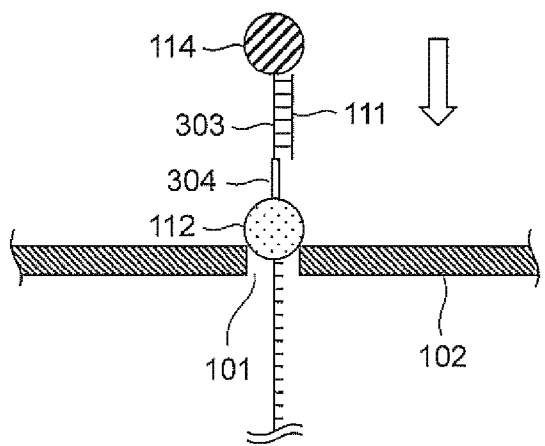
FIG. 9A is a configuration diagram showing the step of analyzing the nucleic acid using the adapter molecule shown in FIG. 7.
Figure 9B:
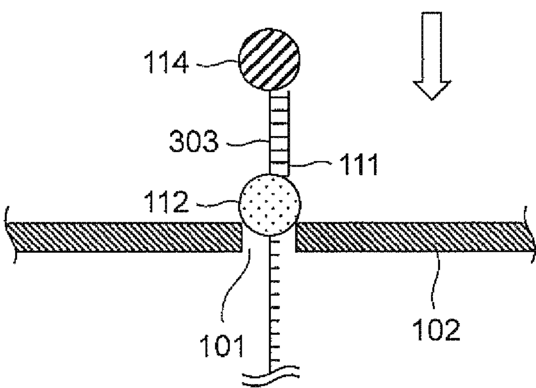
FIG. 9B is a configuration diagram showing the step of analyzing the nucleic acid using the adapter molecule shown in FIG. 7 after the step shown in FIG. 9A.

Due to the potential gradient between the first liquid tank 104A and the second liquid tank 104B, as shown in FIG. 9A, the single-stranded nucleic acid-adapter molecule complex 305 passes through the nanopore 101, and subsequently the DNA polymerase 112 arrives at the nanopore 101. The single-stranded nucleic acid-adapter molecule complex 305 is negatively charged. Therefore, the single-stranded nucleic acid-adapter molecule complex 305 further advances in the downstream direction, and a shape change occurs around the spacer 304. As a result, the DNA polymerase 112 comes into contact with and binds to the 3'terminal of the primer 111 (FIG. 9B). As a result, the DNA polymerase 112 starts the complementary strand synthesis reaction from the 3'terminal of the primer 111 in the direction from the 5'terminal to the 3'terminal. In FIGS. 9A to 9H, a white arrow indicates a potential gradient from a negative electrode toward a positive electrode.

Figure 9C:
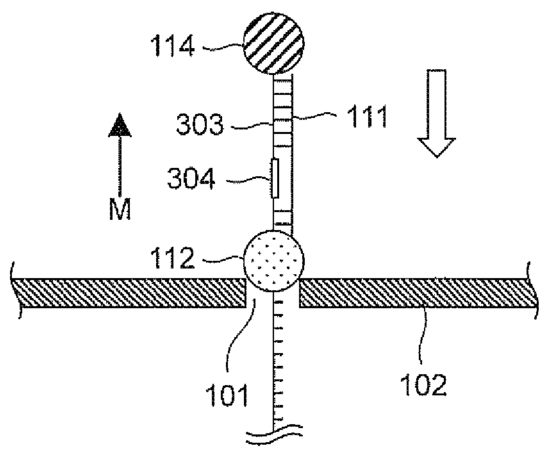
FIG. 9C is a configuration diagram showing the step of analyzing the nucleic acid using the adapter molecule shown in FIG. 7 after the step shown in FIG. 9B.

As shown in FIG. 9C, when the complementary strand synthesis reaction by the DNA polymerase 112 progresses, a force where the single-stranded nucleic acid-adapter molecule complex 305 is pulled by the DNA polymerase 112 is stronger than a force where the single-stranded nucleic acid-adapter molecule complex 305 moves to the second liquid tank 104B side due to the potential gradient. Therefore, the single-stranded nucleic acid-adapter molecule complex 305 is transported against the potential gradient in the direction toward the first liquid tank 104A (direction indicated by arrow M in FIG. 9C). At this time, the base sequence information of the nucleic acid-adapter molecule complex 305 that passes through the nanopore 101 can be acquired.

Figure 9D:
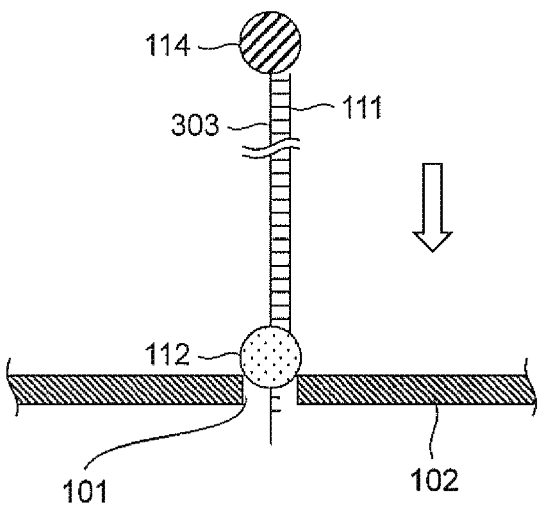
FIG. 9D is a configuration diagram showing the step of analyzing the nucleic acid using the adapter molecule shown in FIG. 7 after the step shown in FIG. 9C.

As shown in FIG. 9D, when the DNA polymerase 112 arrives at the region of the single-stranded nucleic acid region 301B of the nucleic acid-adapter molecule complex 305, the transport operation and sequencing by the DNA polymerase 112 are stopped. At a stage of stopping the transport operation and sequencing by the DNA polymerase 112, the second liquid tank 104B has a stronger positive potential. At the timing at which the second liquid tank 104B has a stronger positive potential, a method of automatically switching between voltages at a predetermined time interval or a method of switching between voltages using the read base sequence information can also be used.

For example, a method of incorporating a characteristic sequence or a region for generating a blocking current different from those of bases (AGCT) into a first adapter molecule 110 and switching between voltages at a stage of reading a signal of the characteristic sequence or the region can be used. Examples of the region for generating a blocking current different from those of bases (AGCT) include a region including a pseudo nucleic acid such as a peptide nucleic acid or an artificial nucleic acid. By reading the signal of the characteristic sequence or the region for generating a blocking current different from those of bases, the reading of the base sequence regarding the nucleic acid 109 ends, and the approach of the end portion of the nucleic acid-adapter molecule complex 305 to the nanopore 101 can be recognized. Accordingly, by switching the applied voltage at this timing, the nucleic acid-adapter molecule complex 305 can be moved in the reverse direction before the end portion of the nucleic acid-adapter molecule complex 305 comes into contact with the nanopore 101.

Figure 9E:
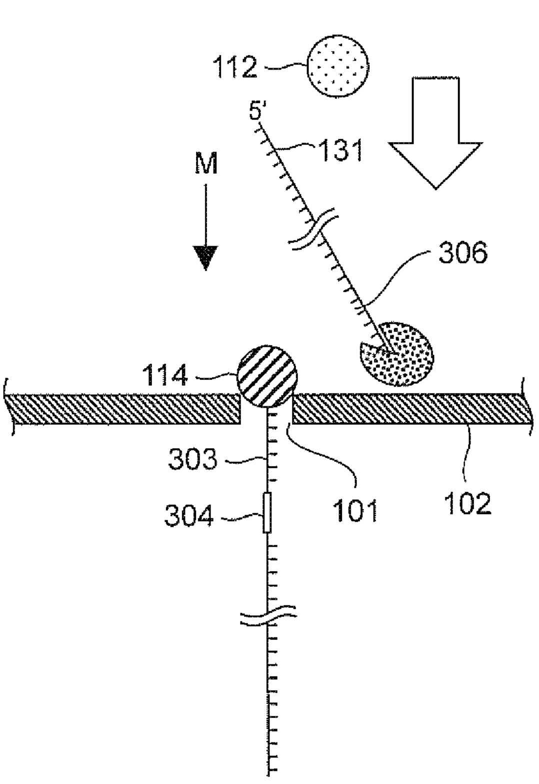
FIG. 9E is a configuration diagram showing the step of analyzing the nucleic acid using the adapter molecule shown in FIG. 7 after the step shown in FIG. 9D.

As a result, as shown in FIG. 9E, the nucleic acid-adapter molecule complex 305 moves to the second liquid tank 104B side due to the potential gradient (direction indicated by the arrow M in FIG. 9E). At this time, a complementary strand 306 of the nucleic acid-adapter molecule complex 305 synthesized by the DNA polymerase 112 is peeled off (unzipped) from the nucleic acid-adapter molecule complex 305, and the DNA polymerase 112 is separated from the nucleic acid-adapter molecule complex 305. In addition, at this time, the degradation inhibition portion 114 abuts against the nanopore 101 such that the nucleic acid-adapter molecule complex 305 can be prevented from falling off to the second liquid tank 104B.

The peeled complementary strand 306 is degraded by the exonuclease 113 as shown in FIG. 9E.

Figures 9F, 9G:
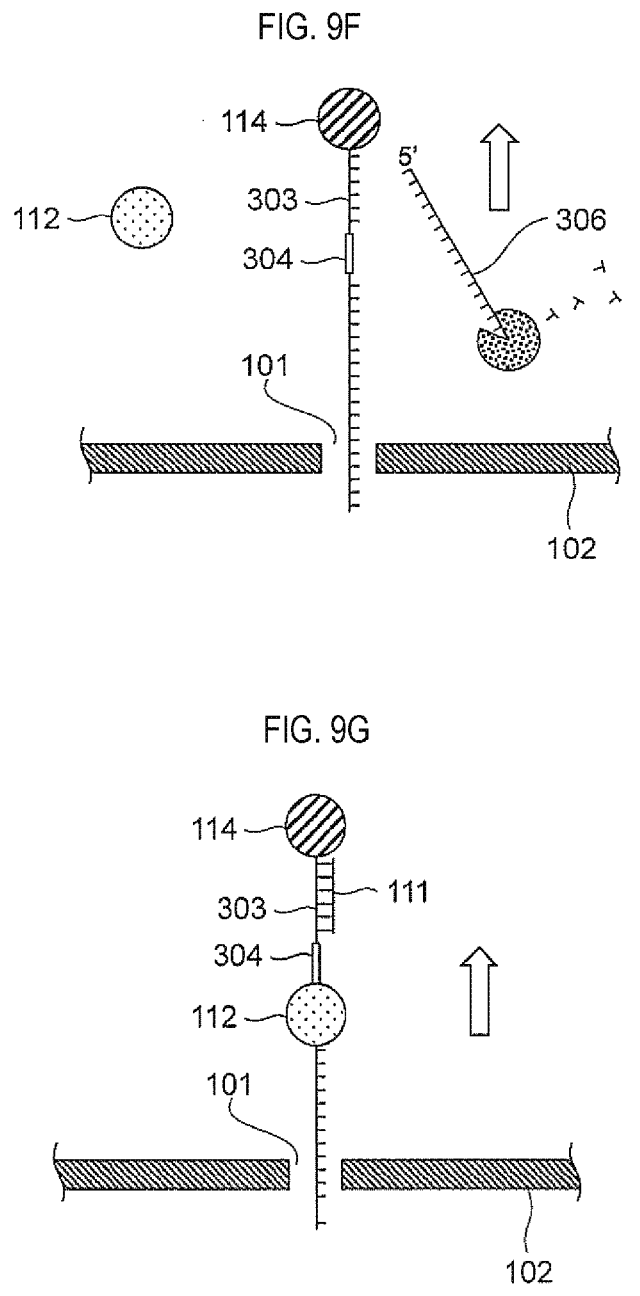

Next, as shown in FIG. 9F, the voltage that is applied to the first electrode 105A and the second electrode 105B is inverted to form a potential gradient that makes the first liquid tank 104A to have a positive potential and makes the second liquid tank 104B to have a negative potential. As a result, the single-stranded nucleic acid-adapter molecule complex 305 can be moved in a direction from the second liquid tank 104B to the first liquid tank 104A through the nanopore 101.

Next, as shown in FIG. 9G, the DNA polymerase 112 that is present in the electrolytic solution 103 filled in the first liquid tank 104A binds to the molecular motor binding portion 302 again, and the primer 111 that is present in the electrolytic solution 103 is hybridized to the primer binding portion 303 again. At this time, the DNA polymerase 112 and the primer 111 may be added to the electrolytic solution 103 filled in the first liquid tank 104A. Next, the voltage that is applied to the first electrode 105A and the second electrode 105B is inverted again to form a potential gradient that makes the first liquid tank 104A to have a negative potential and makes the second liquid tank 104B to have a positive potential. As a result, the primer 111 is hybridized, and the nucleic acid-adapter molecule complex 305 to which the DNA polymerase 112 binds is moved in the direction toward the second liquid tank 104B. As shown in FIG. 9B, a shape change occurs around the spacer 304, and a state where the 3'terminal of the primer 111 is in contact with the DNA polymerase 112 is formed. That is, by repeating FIGS. 9A to 9G, sequencing can be performed per the transport operation by the DNA polymerase 112.

Reference Literature (Nat Nanotechnol. 2010, November; 5(11): 798-806) indicates that the measurement (the diameter of the nanopore 101: 1.4 nm) using the DNA polymerase 112 is performed while applying a voltage of at least 80 mV. In this case, Reference Literature (Nature physics, 5, 347-351, 2009) indicates that a force of about 24 pN is applied. Accordingly, in the embodiment, in order to impart a peel-off preventing function to the degradation inhibition portion 114, it is preferable that the degradation inhibition portion 114 binds to the single-stranded nucleic acid region 301A with a binding force of 24 pN or more assuming that the measurement is performed at a voltage of 80 mV.

As described above, as shown in FIGS. 8A and 8B and FIGS. 9A to 9G, when the base sequence of the nucleic acid 109 to be analyzed is repeatedly read multiple times, the electrolytic solution 103 filled in the first liquid tank 104A includes the endonuclease 113, and the complementary strand 306 synthesized by the DNA polymerase 112 can be degraded by the endonuclease 113 in the first liquid tank 104A. Therefore, the complementary strand 306 synthesized by the DNA polymerase 112 can be prevented from approaching the nanopore 101 and inhibiting the complementary strand synthesis reaction by the DNA polymerase 112 or from blocking the nanopore 101 and inhibiting the transport of the nucleic acid molecule 110. As a result, with the nucleic acid analyzer described above, the base sequence of the nucleic acid 109 to be analyzed can be analyzed with high accuracy.

Third Embodiment

In the embodiment, unlike the adapter molecule according to the first embodiment and the second embodiment, an adapter molecule including a plurality of primer binding portions and molecular motor binding portions corresponding to the primer binding portions will be described. In the adapter molecule and the like described in the embodiment, the same configurations as those of the adapter molecule and the nucleic acid analyzer according to the first embodiment and the second embodiment are represented by the same reference numerals, and the detailed description thereof will not be repeated.

Figure 10:
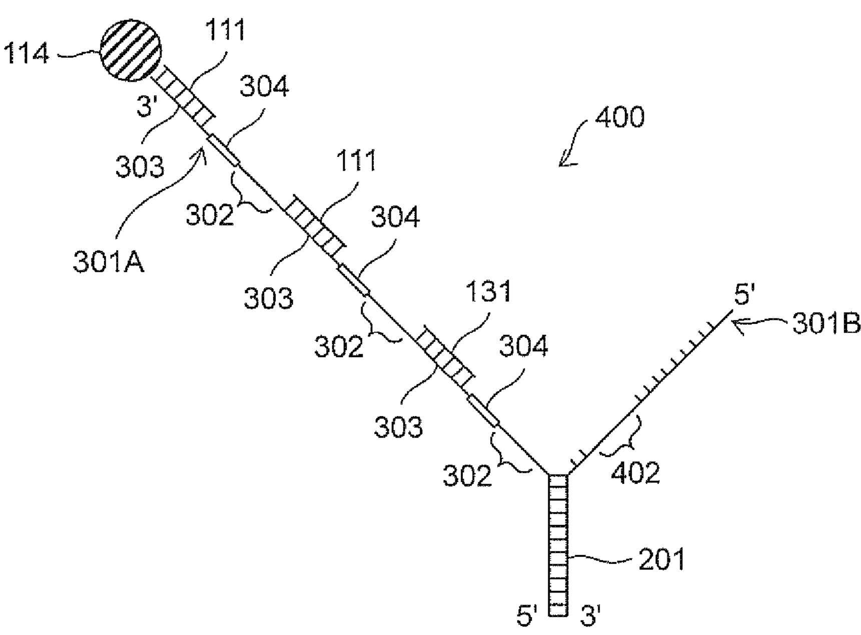
FIG. 10 is a configuration diagram schematically showing another example of the adapter molecule used in the nucleic acid analyzing method to which the present invention is applied.

As shown in FIG. 10, an adapter molecule 400 according to the embodiment includes plural sets including the molecular motor binding portions 302 to which the DNA polymerase 112 is bindable and the primer binding portions 303 where the primer 111 is hybridizable further on the 3'terminal side than the molecular motor binding portion 302. Here, the number of the combinations of the molecular motor binding portions 302 and the primer binding portions 303 is not particularly limited as long as it is plural (2 or more), and can be, for example, 2 to 10 and preferably 2 to 5. The number of the combinations of the molecular motor binding portions 302 and the primer binding portions 303 corresponds to the number of times of reading the base sequence of the nucleic acid 109 to be analyzed. Therefore, the number of times of reading the base sequence of the nucleic acid 109 can also be predetermined such that the number of the combinations of the molecular motor binding portions 302 and the primer binding portions 303 can be set to correspond to the number of times.

In addition, in the adapter molecule 400 according to the embodiment, a molecular motor detachment induction portion 402 is provided in the single-stranded nucleic acid region 301B. The molecular motor detachment induction portion 402 is a region having a characteristic in which a binding force to the DNA polymerase 112 is lower when a binding forces to the nucleic acid 109 and the binding force to the DNA polymerase 112 are compared to each other. The molecular motor detachment induction portion 402 is not particularly limited and can be a region that consists of a carbon chain not including a phosphodiester bond or an abasic sequence. Here, the DNA polymerase 112 binds to a nucleic acid where nucleotide binds to a phosphodiester bond. Accordingly, as the molecular motor detachment induction portion 402, a structure different from a nucleic acid, that is, for example, a chain structure other than a structure to which a monomer binds through a phosphodiester bond can be used. As the molecular motor detachment induction portion 402, a structure not having a base is more preferable. For example, the molecular motor detachment induction portion 402 can be configured with an iSpC3 abasic site. In this case, a phosphate group that is smaller than or equal to the size of the DNA polymerase 112 or more is disposed. Therefore, it is preferable to provide a region where the phosphate group is not present in a length that is more than or equal to the average physical dimension of the DNA polymerase 112. For example, iSp9 or iSp18 can be used. In addition, as the molecular motor detachment induction portion 402, plural types among the above-described examples may be linked regularly or randomly. Further, the molecular motor detachment induction portion 402 is not limited to being configured with the above-described abasic site, and a carbon chain having a given length or polyethylene glycol (PEG) having a given length may also be used. In addition, the molecular motor detachment induction portion 402 may be a modified base having a phosphate group as long as it can suppress and stop the extension reaction by polymerase. Examples of the modified base having a phosphate group include Nitroindole. By using Nitroindole as the molecular motor detachment induction portion 402, the extension reaction of polymerase can be stopped.

A method of analyzing the nucleic acid 109 using the adapter molecule 400 having the above-described configuration will be described using FIGS. 11 to 14.

First, a nucleic acid-adapter molecule complex 401 where the adapter molecule 400 binds to one end portion of the nucleic acid 109 is prepared. The first liquid tank 104A is filled with the electrolytic solution including the nucleic acid-adapter molecule complex 401, the DNA polymerase 112, and the primer 111. As a result, the DNA polymerase 112 binds to each of the plurality of molecular motor binding portions 302 in the adapter molecule 400, and the primer 111 is hybridized to each of the plurality of primer binding portions 303. The primer 111 can also be hybridized to the primer binding portion 303 of the nucleic acid-adapter molecule complex 401 in advance.

Figure 11:
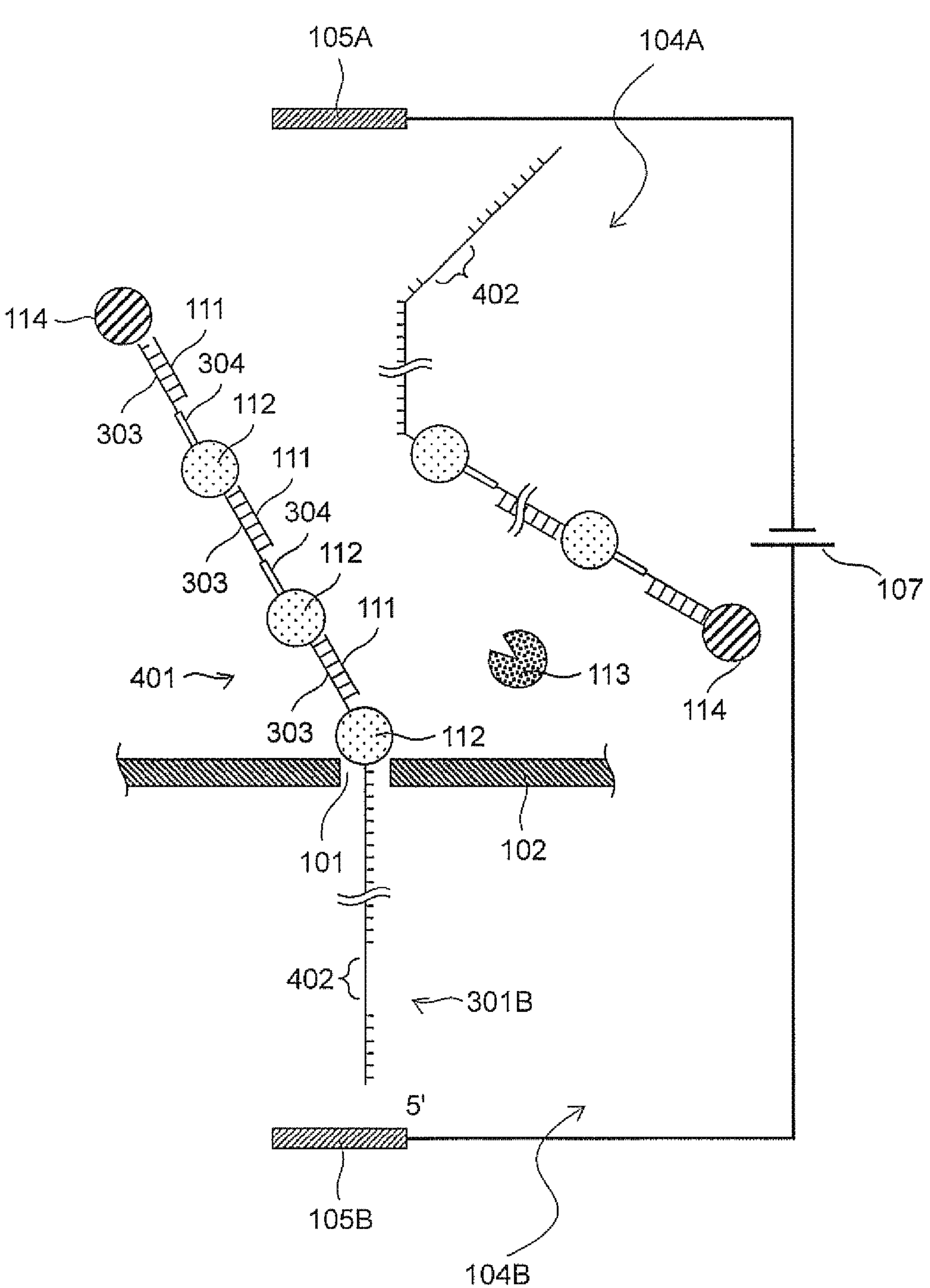
FIG. 11 is a configuration diagram showing the step of analyzing the nucleic acid using the adapter molecule shown in FIG. 10.

Next a voltage is applied between the first electrode 105A and the second electrode 105B to form a potential gradient that makes the first liquid tank 104A side to have a negative potential and makes the second liquid tank 104B to have a positive potential. As a result, as shown in FIG. 11, the end portion of the nucleic acid-adapter molecule complex 401 to which the adapter molecule 400 does not bind moves in the direction toward the nanopore 101 and is introduced into the nanopore 101. Due to the potential gradient between the first liquid tank 104A and the second liquid tank 104B, the nucleic acid-adapter molecule complex 401 moves to the second liquid tank 104B through (via) the nanopore 101. Further, due to the voltage gradient, as shown in FIG. 11, the nucleic acid-adapter molecule complex 401 moves to the second liquid tank 104B through (via) the nanopore 101, and the double-stranded nucleic acid (the double-stranded nucleic acid region 201 and the nucleic acid 109 in the adapter molecule 400) is peeled off (unzipped). Even in this case, the degradation inhibition portion 114 provided at the end portion of the single-stranded nucleic acid region 301A can prevent the nucleic acid-adapter molecule complex 401 from falling off to the second liquid tank 104B.

Due to the potential gradient between the first liquid tank 104A and the second liquid tank 104B, as shown in FIG. 11, the nucleic acid-adapter molecule complex 401 passes through the nanopore 101, and subsequently the DNA polymerase 112 at a position closest to the nucleic acid 109 arrives at the nanopore 101. The single-stranded nucleic acid-adapter molecule complex 401 is negatively charged. Therefore, the single-stranded nucleic acid-adapter molecule complex 401 further advances in the downstream direction, and a shape change occurs around the spacer 304. As a result, the DNA polymerase 112 comes into contact with the 3'terminal of the primer 111, and starts the complementary strand synthesis reaction from the 3'terminal of the primer 111 in the direction from the 5'terminal to the 3'terminal.

When the complementary strand synthesis reaction by the DNA polymerase 112 progresses, a force where the single-stranded nucleic acid-adapter molecule complex 401 is pulled by the DNA polymerase 112 is stronger than a force where the single-stranded nucleic acid-adapter molecule complex 401 moves to the second liquid tank 104B side due to the potential gradient. Therefore, the nucleic acid-adapter molecule complex 401 is transported against the potential gradient in the direction toward the first liquid tank 104A (refer to FIGS. 9C and 9D). At this time, the base sequence information of the nucleic acid-adapter molecule complex 401 that passes through the nanopore 101 can be acquired.

Figure 12:
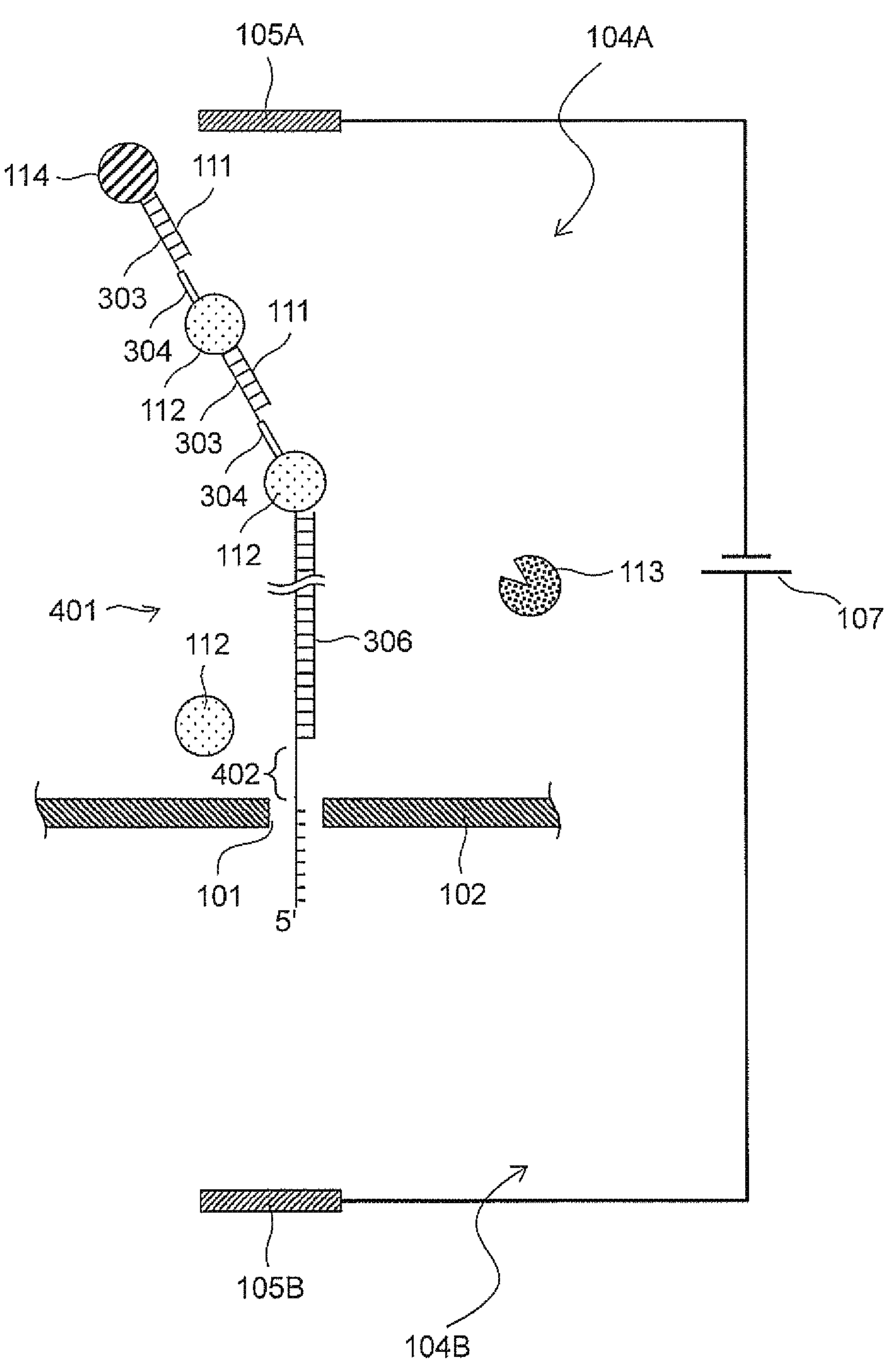
FIG. 12 is a configuration diagram showing the step of analyzing the nucleic acid using the adapter molecule shown in FIG. 10 after the step shown in FIG. 11.

The DNA polymerase 112 continuously transport the nucleic acid-adapter molecule complex 401 in the direction toward the first liquid tank 104A, and when the DNA polymerase 112 arrives at the position of the molecular motor detachment induction portion 402 as shown in FIG. 12, the DNA polymerase 112 is separated from the nucleic acid-adapter molecule complex 401. When the DNA polymerase 112 is separated from the nucleic acid-adapter molecule complex 401, due to the potential gradient between the first liquid tank 104A and the second liquid tank 104B, the nucleic acid-adapter molecule complex 401 including the complementary strand 306 moves in the direction toward the second liquid tank 104B, and the complementary strand 306 is peeled off (unzipped) from the nucleic acid-adapter molecule complex 401.

As described above, by using the adapter molecule 400, the DNA polymerase 112 is easily separated from the nucleic acid-adapter molecule complex 401. Therefore, a treatment of making the second liquid tank 104B to have a stronger positive potential such that the DNA polymerase 112 is forcibly separated and the synthesized complementary strand 306 is peeled off is unnecessary.

Figure 13:
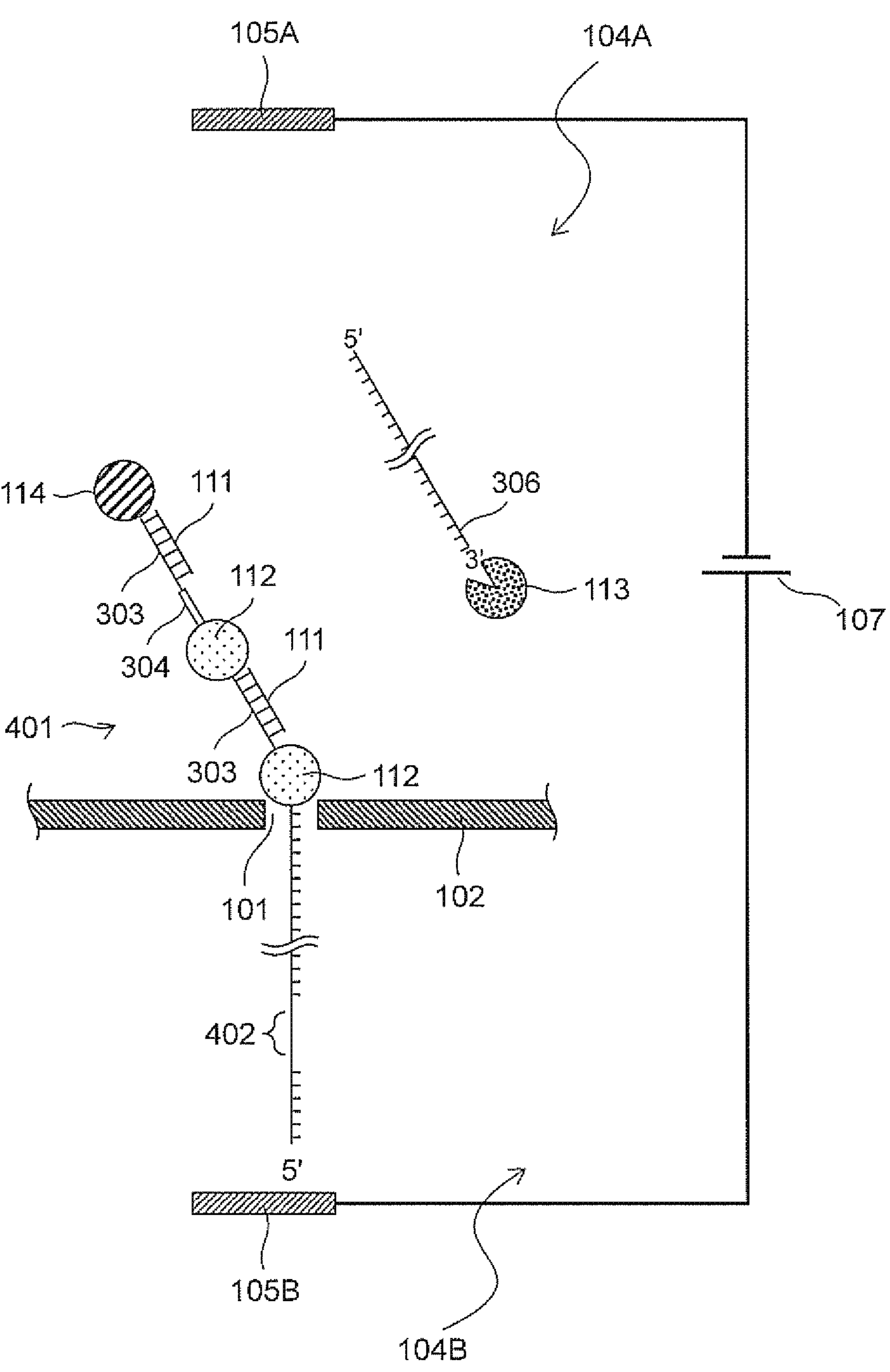
FIG. 13 is a configuration diagram showing the step of analyzing the nucleic acid using the adapter molecule shown in FIG. 10 after the step shown in FIG. 12.
Figure 14:
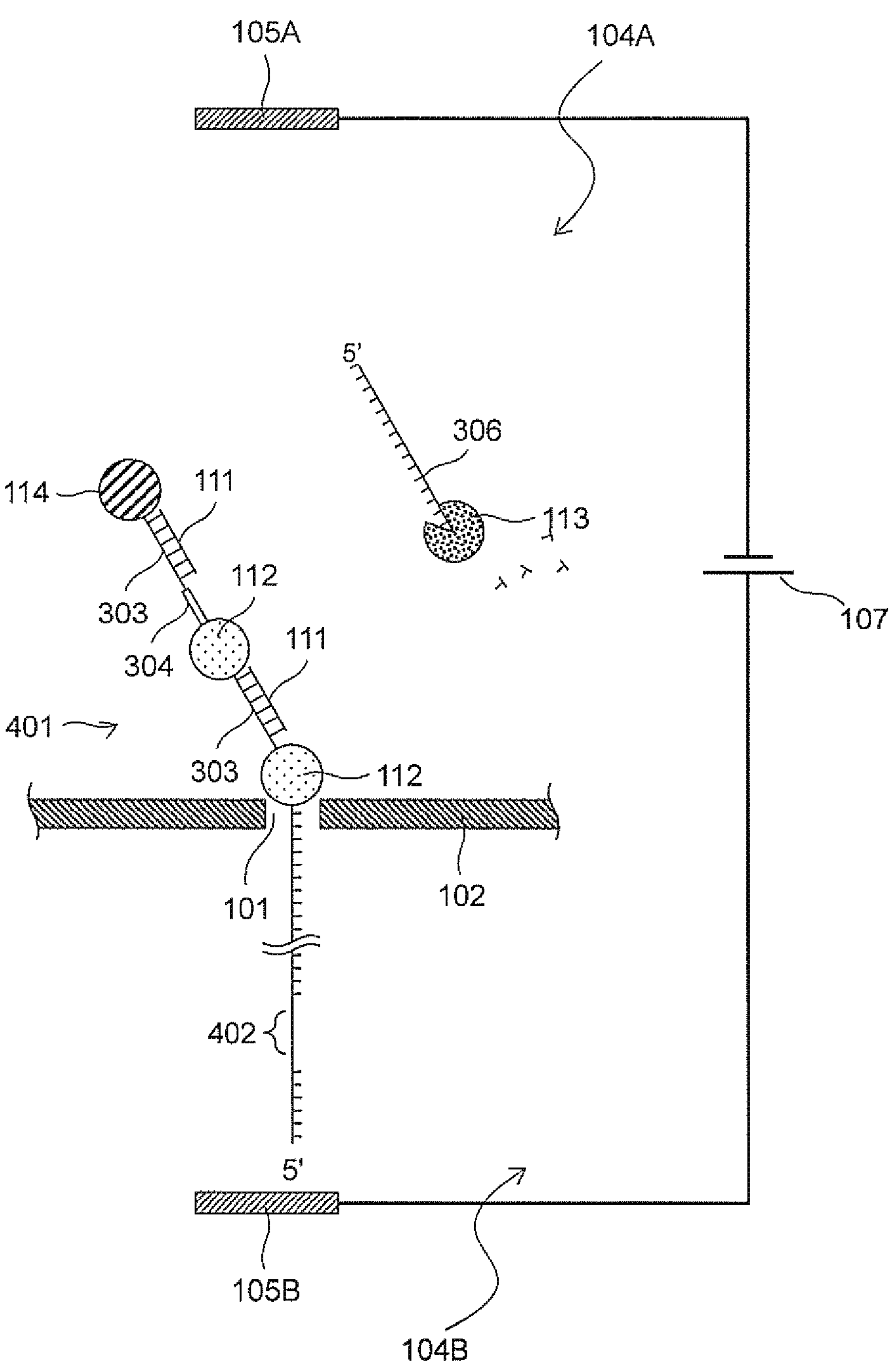
FIG. 14 is a configuration diagram showing the step of analyzing the nucleic acid using the adapter molecule shown in FIG. 10 after the step shown in FIG. 13.

When the complementary strand 306 is peeled off from the nucleic acid-adapter molecule complex 401, the next DNA polymerase 112 arrives at the nanopore 101 as shown in FIG. 13. Due to the potential gradient between the first liquid tank 104A and the second liquid tank 104B, the nucleic acid-adapter molecule complex 401 that is negatively charged further advances in the downstream direction, a shape change occurs around the spacer 304, the DNA polymerase 112 comes into contact with the 3'terminal of the primer 111, and the complementary strand synthesis reaction starts again from the 3'terminal of the primer 111. That is, as shown in FIG. 14, the complementary strand of the nucleic acid-adapter molecule complex 401 is synthesized again by the next DNA polymerase 112, and the nucleic acid-adapter molecule complex 401 is transported again against the potential gradient in the direction toward the first liquid tank 104A. At this time, the base sequence information of the nucleic acid-adapter molecule complex 401 that passes through the nanopore 101 can be acquired again.

The peeled complementary strand 306 is degraded by the exonuclease 113 as shown in FIGS. 13 and 14.

The base sequence information of the nucleic acid 109 can be acquired multiple times corresponding to the number of the sets including the DNA polymerases 112 and the primers 111 binding to the adapter molecule 400 as described above. When the adapter molecule 400 is used, the base sequence information of the nucleic acid 109 can be acquired multiple times through the above-described series of treatments without performing the control of inverting the voltage applied between the first liquid tank 104A and the second liquid tank 104B or the step of binding the DNA polymerase 112 and the primer 111 again after the first measurement. That is, when the adapter molecule 400 is used, the accuracy of reading the base sequence of the nucleic acid 109 can be reliably improved through the reciprocation by the very simple operation.

As described above, as shown in FIGS. 10 to 14, when the base sequence of the nucleic acid 109 to be analyzed is repeatedly read multiple times, the electrolytic solution 103 filled in the first liquid tank 104A includes the endonuclease 113, and the complementary strand 306 synthesized by the DNA polymerase 112 can be degraded by the endonuclease 113 in the first liquid tank 104A. Therefore, the complementary strand 306 synthesized by the DNA polymerase 112 can be prevented from approaching the nanopore 101 and inhibiting the complementary strand synthesis reaction by the DNA polymerase 112 or from blocking the nanopore 101 and inhibiting the transport of the nucleic acid molecule 110. As a result, with the nucleic acid analyzer described above, the base sequence of the nucleic acid 109 to be analyzed can be analyzed with high accuracy.

Fourth Embodiment

This embodiment is an example of a nucleic acid analyzer based on a principle different from that of the nucleic acid analyzers according to the first embodiment to the third embodiment. The nucleic acid analyzers according to the first embodiment to the third embodiment are the nucleic acid analyzers of the so-called nanopore DNA sequencing method. The nucleic acid analyzer according to the embodiment is a device that analyzes the base sequence of a nucleic acid using a so-called single-molecule real-time sequencing method (SMRT) (Schadt et al., Hum. Mol. Genet. (2010) 19 (R2): 227-240).

Figure 15:
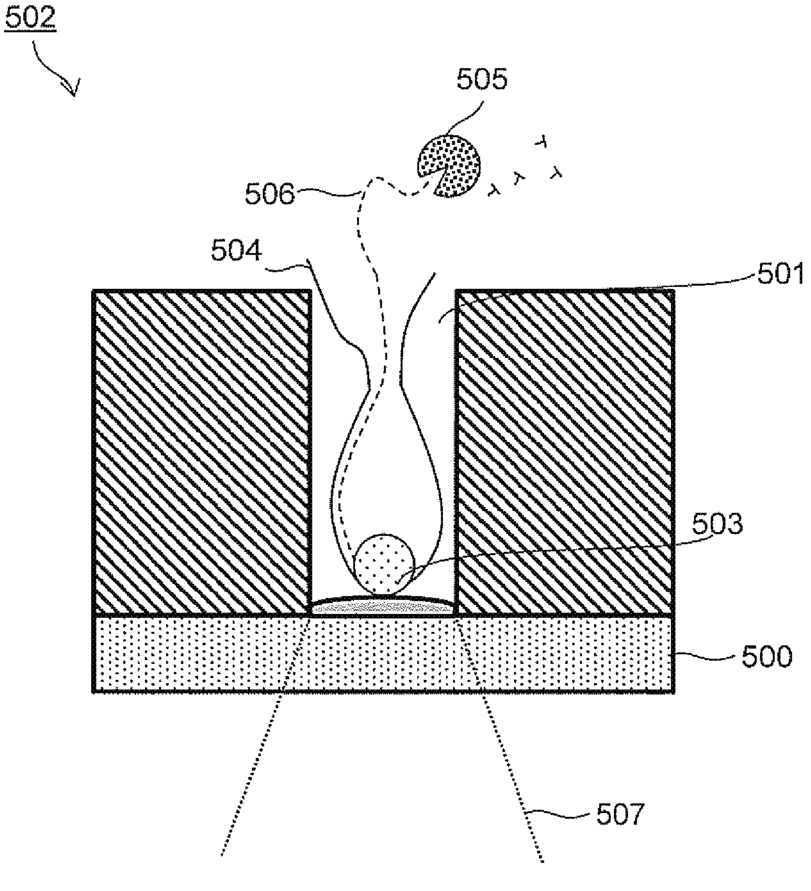
FIG. 15 is a configuration diagram schematically showing another example of the nucleic acid analyzer to which the present invention is applied.

As shown in FIG. 15, the nucleic acid analyzer according to the embodiment includes: a translucent substrate 500; and a cell 502 where a hole 501 called ZMW (zero-mode waveguide) is formed on the substrate 500. Single-molecule DNA polymerase 503 is fixed to the bottom surface of the hole 501. The cell 502 includes a plurality of holes 501.

In the nucleic acid analyzer having the above-described configuration, the cell 502 is filled with a solution including a template nucleic acid 504 that includes a nucleic acid to be analyzed, a primer (not shown), the DNA polymerase 503, fluorescence-labeled nucleotides as a substrate of the DNA polymerase 503 (different fluorescence labels are given to four kinds of nucleotides), and exonuclease 505. As a result, in the cell 502, the primer is hybridized to a predetermined position of the template nucleic acid 504, and the DNA polymerase 503 binds to the template nucleic acid 504 such that a complex is formed. The single-molecule complex is fixed to the bottom surface of the hole 501 through the DNA polymerase 503. In this state, a complementary strand 506 of the template nucleic acid 504 is synthesized by the DNA polymerase 503. In the nucleic acid analyzer, excitation light 507 is irradiated from the bottom surface of the hole 501, and when nucleotide complementary to the template nucleic acid 504 is incorporated into the DNA polymerase 503, fluorescence is emitted from only the fluorescence label binding to the incorporated nucleotide. By detecting this fluorescence, the base sequence of the complementary strand 506 of the template nucleic acid 504 can be determined.

Here, when the nucleic acid analyzer is used, the template nucleic acid 504 having a circular structure may be used, or the template nucleic acid 504 having a chain structure may be used. The circular template nucleic acid 504 can be prepared by linking an adapter molecule having a hairpin structure to each of opposite end portions of the double-stranded nucleic acid to be analyzed. That is, the circular template nucleic acid 504 can be prepared by linking the adapter molecule having a hairpin structure to the opposite end portions of the double-stranded nucleic acid to be analyzed such that the double-stranded region is single-stranded.

In a case where the complementary strand synthesis of the circular template nucleic acid 504 by the DNA polymerase 503 is continued, when the DNA polymerase 503 arrives at the position where the complementary strand 506 is formed, the complementary strand 506 hybridized to the circular template nucleic acid 504 is peeled off, and the new complementary strand 506 is synthesized. In addition, regarding the template nucleic acid 504 having a chain structure, the complementary strand 506 is peeled off, for example, using a method of controlling the reaction temperature, and the new complementary strand 506 is synthesized by the DNA polymerase 503. As a result, in the nucleic acid analyzer, the template nucleic acid 504 including the nucleic acid to be analyzed can be repeatedly read multiple times.

At this time, in the nucleic acid analyzer according to the embodiment, the peeled off complementary strand 506 can be degraded by the exonuclease 505. As a result, the peeled complementary strand 506 can be prevented from approaching the hole 501, and the template nucleic acid 504 can be repeatedly read with high accuracy without inhibiting the complementary strand synthesis reaction by the DNA polymerase 503.

The invention claimed is:

1. A nucleic acid analyzing method comprising the steps of:

synthesizing a complementary strand of a nucleic acid to be analyzed by DNA polymerase in a solution including the nucleic acid to be analyzed, DNA polymerase, nucleotide as a substrate of DNA polymerase, and exonuclease;

determining a sequence of one base in response to the synthesis of one base by the DNA polymerase; and degrading the complementary strand synthesized by DNA polymerase with exonuclease, wherein, in the sequence determination step, the DNA polymerase synthesizes the complementary strand of the nucleic acid to be analyzed in a first liquid tank among the first liquid tank and a second liquid tank that face each other with a membrane having a nanopore interposed therebetween such that the nucleic acid to be analyzed is moved in a direction from the second liquid tank to the first liquid tank through the nanopore to measure a signal generated during the movement of the nucleic acid to be analyzed, and wherein, in the degradation step, the nucleic acid to be analyzed for which the complementary strand is formed is moved in a direction from the first liquid tank to the second liquid tank such that the complementary strand is single-stranded and the single-stranded complementary strand is degraded by exonuclease in the first liquid tank.

2. The nucleic acid analyzing method according to claim 1, wherein, before performing the sequence determination step, preparing a nucleic acid-adapter molecule complex where an adapter molecule directly or indirectly binds to at least one end portion of the nucleic acid to be analyzed is provided such that degradation of the nucleic acid to be analyzed by the exonuclease is inhibited by the adapter molecule.

3. The nucleic acid analyzing method according to claim 2 wherein the adapter molecule includes a double-stranded nucleic acid region that includes one end portion directly or indirectly binding to the nucleic acid to be analyzed and consists of base sequences complementary to each other, a pair of single-stranded nucleic acid regions that are linked to another end portion of the double-stranded nucleic acid region different from the one end portion and consist of base sequences non-complementary to each other, and a degradation inhibition portion that is provided on one of the pair of single-stranded nucleic acid regions and inhibits the nucleic acid degradation reaction by the exonuclease, and wherein, among the pair of single-stranded nucleic acid regions, a single-stranded nucleic acid region where the degradation inhibition portion is not provided is introduced into the second liquid tank through the nanopore.

4. The nucleic acid analyzing method according to claim 3, wherein, among the pair of single-stranded nucleic acid regions, a single-stranded nucleic acid region having an end portion of 3'terminal includes a molecular motor binding portion to which DNA polymerase is bindable, and wherein the DNA polymerase binding to the molecular motor binding portion synthesizes the complementary strand.

5. The nucleic acid analyzing method according to claim 4, further comprising the step of:

providing a primer, wherein the single-stranded nucleic acid region including the molecular motor binding portion includes a primer binding portion to which the primer is hybridizable further on the 3'terminal side than the molecular motor binding portion, and wherein the DNA polymerase binding to the molecular motor binding portion synthesizes the complementary strand from the primer hybridized to the primer binding portion.

6. The nucleic acid analyzing method according to claim 4, wherein the single-stranded nucleic acid region includes plural sets of the molecular motor binding portion and a primer binding portion to which a primer is hybridizable further on the 3'terminal side than the molecular motor binding portion, and wherein, by repeating an operation in which a DNA polymerase closest to the nanopore among DNA polymerases binding to the molecular motor binding portion synthesizes the complementary strand from the primer hybridized to the primer binding portion such that the nucleic acid-adapter molecule complex is moved from the second liquid tank to the first liquid tank, subsequently the nucleic acid-adapter molecule complex including the complementary strand is moved from the first liquid tank to the second liquid tank to peel off the complementary strand, and the DNA polymerase closest to the nanopore synthesizes the complementary strand again such that the nucleic acid-adapter molecule complex is moved from the second liquid tank to the first liquid tank, the endonuclease degrades the peeled complementary strand in the first liquid tank.

7. The nucleic acid analyzing method according to claim 4, wherein a spacer to which the DNA polymerase is not bindable is provided between the molecular motor binding portion and a primer binding portion.

8. The nucleic acid analyzing method according to claim 3, wherein, among the pair of single-stranded nucleic acid regions, a single-stranded nucleic acid region having an end portion of 5'terminal includes a molecular motor detachment induction portion where a binding force to DNA polymerase is lower than a binding force to a nucleic acid, and wherein the DNA polymerase synthesizes the complementary strand from a primer hybridized to a primer binding portion such that the nucleic acid-adapter molecule complex is moved from the second liquid tank to the first liquid tank and the DNA polymerase is separated in the molecular motor detachment induction portion of the nucleic acid-adapter molecule complex.

* * * * *